US012662699B2

(12) United States Patent
Kühnemund et al.

(10) Patent No.: US 12,662,699 B2
(45) Date of Patent: *Jun. 23, 2026

(54) METHOD OF DETECTING AN ANALYTE

(71) Applicant: 10x Genomics, Inc., Pleasanton, CA (US)

(72) Inventors: Malte Kühnemund, Stockholm (SE); Mats Nilsson Bernitz, Drottningholm (SE); Jessica Östlin, Stocksund (SE)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/127,451

(22) Filed: Dec. 18, 2020

(65) Prior Publication Data

US 2021/0198727 A1 Jul. 1, 2021

(30) Foreign Application Priority Data

Dec. 20, 2019 (GB) ..................................... 1919029

(51) Int. Cl.
C12Q 1/68 (2018.01)
C12Q 1/6841 (2018.01)
C12Q 1/6844 (2018.01)
C12Q 1/6886 (2018.01)

(52) U.S. Cl.
CPC ......... C12Q 1/6841 (2013.01); C12Q 1/6844 (2013.01); C12Q 1/6886 (2013.01); C12Q 2600/156 (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,883,867 A | 11/1989 | Lee |
| 4,965,188 A | 10/1990 | Mullis et al. |
| 5,321,130 A | 6/1994 | Yue et al. |
| 5,340,716 A | 8/1994 | Ullman et al. |
| 5,410,030 A | 4/1995 | Yue et al. |
| 5,436,134 A | 7/1995 | Haugland et al. |
| 5,512,462 A | 4/1996 | Cheng |
| 5,582,977 A | 12/1996 | Yue et al. |
| 5,635,352 A | 6/1997 | Urdea et al. |
| 5,658,751 A | 8/1997 | Yue et al. |
| 5,695,940 A | 12/1997 | Drmanac et al. |
| 5,863,753 A | 1/1999 | Haugland et al. |
| 5,989,823 A | 11/1999 | Jayasena et al. |
| 6,117,635 A | 9/2000 | Nazarenko et al. |
| 6,248,526 B1 | 6/2001 | Weimer |
| 6,306,597 B1 | 10/2001 | Macevicz |
| 6,326,145 B1 | 12/2001 | Whitcombe et al. |
| 6,346,384 B1 | 2/2002 | Pollner |

| | | | |
|---|---|---|---|
| 6,534,266 B1 | 3/2003 | Singer |
| 7,255,994 B2 | 8/2007 | Lao |
| 7,264,929 B2 | 9/2007 | Rothberg et al. |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,632,641 B2 | 12/2009 | Dirks et al. |
| 7,655,898 B2 | 2/2010 | Miller |
| 7,721,721 B1 | 5/2010 | Kronengold et al. |
| 7,893,227 B2 | 2/2011 | Wu et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,198,031 B2 | 6/2012 | Chan-Yui et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |

(Continued)

FOREIGN PATENT DOCUMENTS

| | | |
|---|---|---|
| EP | 1997909 | 12/2008 |
| WO | WO-1999/049079 | 9/1999 |

(Continued)

OTHER PUBLICATIONS

Bi et al. 2013. Hybridization chain reaction-based branched rolling circle amplification for chemiluminescence detection of DNA methylation. Chem. Commun., vol. 49, p. 6906-6908.*
Song et al. Ultrasensitive detection of nucleic acids by template enhanced hybridization followed by rolling circle amplification and catalytic hairpin assembly. Chem Commun., vol. 51(12), p. 2392-2395, (2015).*
Chemeris et al., "Real-time hybridization chain reaction," Dokl Biochem Biophys. (2008) 419: 53-55.
Choi et al., "Programmable in situ amplification for multiplexed imaging of mRNA expression," Nat Biotechnol. (2010) 28(11): 1208-1212.

(Continued)

Primary Examiner — Suryaprabha Chunduru
(74) Attorney, Agent, or Firm — MORRISON & FOERSTER LLP

(57) ABSTRACT

The present disclosure in some aspects relates to methods for detecting a target analyte in a sample by a method comprising rolling circle amplification (RCA) and hybridisation chain reaction (HCR).

21 Claims, 8 Drawing Sheets
(6 of 8 Drawing Sheet(s) Filed in Color)
Specification includes a Sequence Listing.

(56) References Cited

U.S. PATENT DOCUMENTS

| | | | |
|---|---|---|---|
| 8,632,975 B2 | 1/2014 | Vander Horn et al. | |
| 8,658,361 B2 | 2/2014 | Wu et al. | |
| 8,771,950 B2 | 7/2014 | Church et al. | |
| 8,986,926 B2 | 3/2015 | Ferree et al. | |
| 9,201,063 B2 | 12/2015 | Sood et al. | |
| 9,273,349 B2 | 3/2016 | Nguyen et al. | |
| 9,371,563 B2 | 6/2016 | Geiss et al. | |
| 9,371,598 B2 | 6/2016 | Chee | |
| 9,376,717 B2 | 6/2016 | Gao et al. | |
| 9,541,504 B2 | 1/2017 | Hoyt | |
| 9,551,032 B2 | 1/2017 | Landegren et al. | |
| 9,624,538 B2 | 4/2017 | Church et al. | |
| 9,650,406 B2 | 5/2017 | Zhou et al. | |
| 9,714,446 B2 | 7/2017 | Webster et al. | |
| 9,714,937 B2 | 7/2017 | Dunaway | |
| 9,727,810 B2 | 8/2017 | Fodor et al. | |
| 9,778,155 B2 | 10/2017 | Gradinaru et al. | |
| 9,783,841 B2 | 10/2017 | Nolan et al. | |
| 9,909,167 B2 | 3/2018 | Samusik et al. | |
| 10,032,064 B2 | 7/2018 | Hoyt | |
| 10,059,990 B2 | 8/2018 | Boyden et al. | |
| 10,126,242 B2 | 11/2018 | Miller et al. | |
| 10,179,932 B2 | 1/2019 | Church et al. | |
| 10,227,639 B2 | 3/2019 | Levner et al. | |
| 10,246,700 B2 | 4/2019 | Dunaway et al. | |
| 10,266,888 B2 | 4/2019 | Daugharthy et al. | |
| 10,267,808 B2 | 4/2019 | Cai | |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,370,698 B2 | 8/2019 | Nolan et al. | |
| 10,415,080 B2 | 9/2019 | Dunaway et al. | |
| 10,457,980 B2 | 10/2019 | Cai et al. | |
| 10,465,235 B2 | 11/2019 | Gullberg et al. | |
| 10,494,662 B2 | 12/2019 | Church et al. | |
| 10,495,554 B2 | 12/2019 | Deisseroth et al. | |
| 10,501,777 B2 | 12/2019 | Beechem et al. | |
| 10,501,791 B2 | 12/2019 | Church et al. | |
| 10,510,435 B2 | 12/2019 | Cai et al. | |
| 10,526,649 B2 | 1/2020 | Chen et al. | |
| 10,545,075 B2 | 1/2020 | Deisseroth et al. | |
| 10,580,128 B2 | 3/2020 | Miller | |
| 10,640,816 B2 | 5/2020 | Beechem et al. | |
| 10,640,826 B2 | 5/2020 | Church et al. | |
| 10,669,569 B2 | 6/2020 | Gullberg et al. | |
| 10,746,981 B2 | 8/2020 | Tomer et al. | |
| 10,774,372 B2 | 9/2020 | Chee et al. | |
| 10,774,374 B2 | 9/2020 | Frisén et al. | |
| 10,794,802 B2 | 10/2020 | Gradinaru et al. | |
| 10,802,262 B2 | 10/2020 | Tomer et al. | |
| 10,815,519 B2 | 10/2020 | Husain et al. | |
| 10,829,814 B2 | 11/2020 | Fan et al. | |
| 10,844,426 B2 | 11/2020 | Daugharthy et al. | |
| 10,858,698 B2 | 12/2020 | Church et al. | |
| 10,872,679 B2 | 12/2020 | Cai et al. | |
| 10,964,001 B2 | 3/2021 | Miller | |
| 11,174,281 B1 | 11/2021 | Graham et al. | |
| 11,287,422 B2 | 3/2022 | Previte et al. | |
| 11,434,525 B2 | 9/2022 | Glezer | |
| 11,459,603 B2 | 10/2022 | Tyagi et al. | |
| 11,499,185 B2 | 11/2022 | Vijayan et al. | |
| 11,643,679 B2 | 5/2023 | Glezer et al. | |
| 11,999,999 B2 | 6/2024 | Ju et al. | |
| 2006/0234261 A1 | 10/2006 | Pierce et al. | |
| 2011/0223585 A1 | 9/2011 | Gullberg et al. | |
| 2012/0270214 A1* | 10/2012 | Bernitz | C12Q 1/6886 |
| | | | 435/6.11 |
| 2013/0288249 A1 | 10/2013 | Gullbert | |
| 2013/0323729 A1 | 12/2013 | Landegren et al. | |
| 2016/0108458 A1 | 4/2016 | Frei et al. | |
| 2016/0305856 A1 | 10/2016 | Boyden et al. | |
| 2016/0376642 A1 | 12/2016 | Landegren et al. | |
| 2017/0009278 A1* | 1/2017 | Söderberg | G01N 33/54306 |
| 2017/0029872 A1 | 2/2017 | Bhattacharyya et al. | |
| 2017/0081489 A1 | 3/2017 | Rodriques et al. | |
| 2017/0101672 A1 | 4/2017 | Luo et al. | |
| 2017/0220733 A1 | 8/2017 | Zhuang et al. | |
| 2017/0253918 A1 | 9/2017 | Kohman | |
| 2018/0010166 A1* | 1/2018 | Pierce | C12Q 1/6816 |
| 2018/0052081 A1 | 2/2018 | Kohman | |
| 2018/0080876 A1 | 3/2018 | Rockel et al. | |
| 2018/0208967 A1 | 7/2018 | Larman et al. | |
| 2018/0237864 A1 | 8/2018 | Imler et al. | |
| 2018/0320226 A1 | 11/2018 | Church et al. | |
| 2019/0017106 A1 | 1/2019 | Frisen et al. | |
| 2019/0032128 A1 | 1/2019 | Chen et al. | |
| 2019/0055594 A1 | 2/2019 | Samusik et al. | |
| 2019/0112599 A1 | 4/2019 | Church et al. | |
| 2019/0119735 A1 | 4/2019 | Deisseroth et al. | |
| 2019/0155835 A1 | 5/2019 | Daugharthy et al. | |
| 2019/0161796 A1 | 5/2019 | Hauling et al. | |
| 2019/0177718 A1 | 6/2019 | Church et al. | |
| 2019/0194709 A1 | 6/2019 | Church et al. | |
| 2019/0218608 A1 | 7/2019 | Daugharthy et al. | |
| 2019/0249248 A1 | 8/2019 | Beechem et al. | |
| 2019/0264270 A1 | 8/2019 | Zhuang et al. | |
| 2019/0271028 A1 | 9/2019 | Khafizov et al. | |
| 2019/0276881 A1 | 9/2019 | Zhuang et al. | |
| 2019/0339203 A1 | 11/2019 | Miller et al. | |
| 2020/0010891 A1 | 1/2020 | Beechem et al. | |
| 2020/0071751 A1 | 3/2020 | Daugharthy et al. | |
| 2020/0123597 A1 | 4/2020 | Daniel | |
| 2020/0140920 A1 | 5/2020 | Pierce et al. | |
| 2020/0224243 A1 | 7/2020 | Desai et al. | |
| 2020/0224244 A1 | 7/2020 | Nilsson et al. | |
| 2020/0239946 A1 | 7/2020 | Dewal | |
| 2020/0332368 A1 | 10/2020 | Ferree et al. | |
| 2020/0354774 A1 | 11/2020 | Church et al. | |
| 2020/0354782 A1 | 11/2020 | Dewal | |
| 2020/0362398 A1 | 11/2020 | Kishi et al. | |
| 2020/0393343 A1 | 12/2020 | Kennedy-Darling et al. | |
| 2021/0017587 A1 | 1/2021 | Cai et al. | |
| 2021/0115504 A1 | 4/2021 | Cai et al. | |
| 2021/0238662 A1 | 8/2021 | Bava | |
| 2021/0238674 A1 | 8/2021 | Bava | |
| 2021/0254140 A1 | 8/2021 | Stahl et al. | |
| 2021/0262018 A1 | 8/2021 | Bava et al. | |
| 2021/0277460 A1 | 9/2021 | Bava | |
| 2021/0340621 A1 | 11/2021 | Daugharthy et al. | |
| 2021/0388423 A1 | 12/2021 | Bava et al. | |
| 2021/0388424 A1 | 12/2021 | Bava | |
| 2022/0049302 A1 | 2/2022 | Daugharthy et al. | |
| 2022/0049303 A1 | 2/2022 | Busby et al. | |
| 2022/0083832 A1 | 3/2022 | Shah | |
| 2022/0084628 A1 | 3/2022 | Shah | |
| 2022/0084629 A1 | 3/2022 | Shah | |
| 2022/0136049 A1 | 5/2022 | Bava et al. | |
| 2022/0186300 A1 | 6/2022 | Bava | |
| 2022/0195498 A1 | 6/2022 | Kuhnemund et al. | |
| 2022/0213529 A1 | 7/2022 | Kuhnemund et al. | |
| 2022/0228200 A1 | 7/2022 | Bava | |
| 2022/0235403 A1 | 7/2022 | Costa | |
| 2022/0282306 A1 | 9/2022 | Bava et al. | |
| 2022/0282316 A1 | 9/2022 | Bava | |
| 2022/0282319 A1 | 9/2022 | Verheyen | |
| 2022/0372570 A1 | 11/2022 | Costa | |
| 2022/0380838 A1 | 12/2022 | Kuhnemund et al. | |
| 2022/0403458 A1 | 12/2022 | Bava | |
| 2023/0002808 A1 | 1/2023 | Mignardi | |
| 2023/0012607 A1 | 1/2023 | Kuhnemund et al. | |
| 2023/0013775 A1 | 1/2023 | Chen et al. | |
| 2023/0015226 A1 | 1/2023 | Chen et al. | |
| 2023/0026886 A1 | 1/2023 | Chen | |
| 2023/0031305 A1 | 2/2023 | Hernandez Neuta et al. | |
| 2023/0031996 A1 | 2/2023 | Hernandez Neuta et al. | |
| 2023/0035685 A1 | 2/2023 | Hernandez Neuta et al. | |
| 2023/0037182 A1 | 2/2023 | Bava et al. | |
| 2023/0039148 A1 | 2/2023 | Verheyen | |
| 2023/0041485 A1 | 2/2023 | Hernandez Neuta et al. | |
| 2023/0044650 A1 | 2/2023 | Dockter | |
| 2023/0057571 A1 | 2/2023 | Costa et al. | |
| 2023/0061542 A1 | 3/2023 | Kuhnemund | |
| 2023/0084407 A1 | 3/2023 | Hernandez Neuta et al. | |
| 2023/0159997 A1 | 5/2023 | Belhocine et al. | |

(56) References Cited

U.S. PATENT DOCUMENTS

| | | | |
|---|---|---|---|
| 2023/0160794 A1 | 5/2023 | Dockter et al. | |
| 2023/0183787 A1 | 6/2023 | Bava et al. | |
| 2023/0242974 A1 | 8/2023 | Costa et al. | |
| 2023/0279465 A1 | 9/2023 | He et al. | |
| 2023/0279475 A1 | 9/2023 | Kuhnemund et al. | |
| 2023/0279480 A1 | 9/2023 | Kuhnemund | |
| 2023/0287478 A1 | 9/2023 | Bava | |
| 2023/0314327 A1 | 10/2023 | Hoffman | |
| 2023/0314328 A1 | 10/2023 | Costa | |
| 2023/0323427 A1 | 10/2023 | Schnall-Levin | |
| 2023/0323430 A1 | 10/2023 | Shastry | |
| 2023/0323437 A1 | 10/2023 | Chen et al. | |
| 2023/0374573 A1 | 11/2023 | Qian et al. | |
| 2023/0374580 A1 | 11/2023 | Costa | |
| 2023/0416821 A1 | 12/2023 | Bava et al. | |
| 2024/0002902 A1 | 1/2024 | Jakobsen et al. | |
| 2024/0026426 A1 | 1/2024 | Bava | |
| 2024/0026427 A1 | 1/2024 | Kuhnemund et al. | |
| 2024/0026439 A1 | 1/2024 | Sasaki | |
| 2024/0026448 A1 | 1/2024 | Costa | |
| 2024/0035070 A1 | 2/2024 | Christopherson | |
| 2024/0035071 A1 | 2/2024 | Delaney et al. | |
| 2024/0035072 A1 | 2/2024 | Christopherson | |
| 2024/0043910 A1 | 2/2024 | Shastry | |
| 2024/0043914 A1 | 2/2024 | Chen et al. | |
| 2024/0060119 A1 | 2/2024 | Bava | |
| 2024/0084373 A1 | 3/2024 | Shastry | |
| 2024/0084378 A1 | 3/2024 | Marks et al. | |
| 2024/0101978 A1 | 3/2024 | Boghospor et al. | |
| 2024/0132938 A1 | 4/2024 | Kuhnemund | |
| 2024/0141418 A1 | 5/2024 | Mielinis | |
| 2024/0150816 A1 | 5/2024 | Feng et al. | |
| 2024/0158852 A1 | 5/2024 | Belhocine et al. | |
| 2024/0167081 A1 | 5/2024 | Bava et al. | |
| 2024/0175082 A1 | 5/2024 | Costa | |
| 2024/0175083 A1 | 5/2024 | Bava et al. | |
| 2024/0191297 A1 | 6/2024 | Christopherson et al. | |
| 2024/0209330 A1 | 6/2024 | Shastry et al. | |
| 2024/0218424 A1 | 7/2024 | Costa et al. | |
| 2024/0218437 A1 | 7/2024 | Belhocine et al. | |
| 2024/0263219 A1 | 8/2024 | Kuhnemund | |
| 2024/0263220 A1 | 8/2024 | Olofsson | |
| 2024/0264155 A1 | 8/2024 | Costa | |

FOREIGN PATENT DOCUMENTS

| | | | | |
|---|---|---|---|---|
| WO | WO-2001/061037 | 8/2001 | | |
| WO | WO-2003/012119 | 7/2002 | | |
| WO | WO-2005/070630 | 8/2005 | | |
| WO | WO-2005/111236 | 11/2005 | | |
| WO | WO-2016/016450 | 2/2016 | | |
| WO | WO-2016/016452 | 2/2016 | | |
| WO | WO-2017/143155 | 8/2017 | | |
| WO | WO-2018175779 A1 * | 9/2018 | ............. | C12N 15/11 |
| WO | WO-2018217905 A1 * | 11/2018 | ............. | C12N 15/11 |
| WO | WO-2019/199579 | 10/2019 | | |
| WO | WO-2020/076976 | 4/2020 | | |
| WO | WO-2020/076979 | 4/2020 | | |
| WO | WO-2020/096687 | 5/2020 | | |
| WO | WO-2020/099640 | 5/2020 | | |
| WO | WO-2020/117914 | 6/2020 | | |
| WO | WO 2020/123316 | 6/2020 | | |
| WO | WO-2020/123742 | 6/2020 | | |
| WO | WO-2020/142490 | 7/2020 | | |
| WO | WO-2020/240025 | 12/2020 | | |
| WO | WO-2020/254519 | 12/2020 | | |
| WO | WO 2021/123282 | 6/2021 | | |
| WO | WO 2021/123286 | 6/2021 | | |
| WO | WO 2021/138676 | 7/2021 | | |
| WO | WO 2021/155063 | 8/2021 | | |
| WO | WO 2021/168326 | 8/2021 | | |
| WO | WO 2023/108139 | 6/2023 | | |
| WO | WO 2023/141476 | 7/2023 | | |
| WO | WO 2023/172915 | 9/2023 | | |
| WO | WO 2023/192302 | 10/2023 | | |
| WO | WO 2024/148300 | 7/2024 | | |

OTHER PUBLICATIONS

Choi et al., "Next-generation in situ hybridization chain reaction: higher gain, lower cost, greater durability," ACS Nano. (2014) 8(5): 4284-94.

Choi et al., "Third-generation in situ hybridization chain reaction: multiplexed, quantitative, sensitive, versatile, robust," Development. (2018) 6;145(12): dev165753.

Dirks et al., "Triggered amplification by hybridization chain reaction," Proc Natl Acad Sci USA. (2004) 101(43): 15275-15278.

Duose et al., "Configuring robust DNA strand displacement reactions for in situ molecular analyses," Nucleic Acids Res. (2012) 40(7): 3289-3298.

Forcucci et al., "All-plastic miniature fluorescence microscope for point-of-care readout of bead-based bioassays," J Biomed Opt. (2015) 20(10): 105010.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Grundberg et al., "In situ mutation detection and visualization of intratumor heterogeneity for cancer research and diagnostics," Oncotarget. (2013) 4(12): 2407-2418.

Heid et al., "Real time quantitative PCR," Genome Res. (1996) 6(10): 986-94.

Holland et al., "Detection of specific polymerase chain reaction product by utilizing the 5'----3' exonuclease activity of Thermus aquaticus DNA polymerase," Proc Natl Acad Sci USA. (1991) 88(16): 7276-7280.

Ke et al., "In situ sequencing for RNA analysis in preserved tissue and cells," Nat Methods. (2013) 10(9):857-60.

Lee et al., "Allelic discrimination by nick-translation PCR with fluorogenic probes," Nucleic Acids Res. (1993) 21(16): 3761-3766.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

McGinn et al., "New technologies for DNA analysis—a review of the READNA Project," N Biotechnol. (2016) 33(3): 311-30. doi: 10.1016/j.nbt.2015.10.003.

Nazarenko et al., "A closed tube format for amplification and detection of DNA based on energy transfer," Nucleic Acids Res. (1997) 25(12): 2516-21.

Niu et al., "Fluorescence detection for DNA using hybridization chain reaction with enzyme-amplification," Chem Commun (Camb). (2010) 46(18): 3089-91.

Payne et al. "In situ genome sequencing resolves DNA sequence and structure in intact biological samples," Science. (2021) 371(6532): eaay3446. doi: 10.1126/science.aay3446. Epub Dec. 31, 2020.

Raj et al., "Imaging individual mRNA molecules using multiple singly labeled probes," Nat Methods. (2008) 5(10): 877-879.

Rajeswari et al., "Multiple pathogen biomarker detection using an encoded bead array in droplet PCR," J Microbiol Methods. (2017) 139: 22-28.

Rouhanifard et al. "ClampFISH detects individual nucleic acid molecules using click chemistry-based amplification," Nat Biotechnol. (2018) 17 pages. doi: 10.1038/nbt.4286.

Shah et al., "In situ transcription profiling of single cells reveals spatial organization of cells in the mouse hippocampus," Neuron. (2016) 92(2): 342-357.

Song et al., "Hybridization chain reaction-based aptameric system for the highly selective and sensitive detection of protein," Analyst. (2012) 137(6):1396-1401.

Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.

(56) References Cited

OTHER PUBLICATIONS

Tyagi et al., "Molecular Beacons: Probes that Fouresce upon Hybridization," Nature Biotechnology. (1996) 14:303-308.

Wählby et al., "Sequential immunofluorescence staining and image analysis for detection of large Nos. of antigens in individual cell nuclein," Cytometry. (2002) 47(1): 32-41.

Whitcombe et al., "Detection of PCR products using self-probing amplicons and fluorescence," Nat Biotechnol. (1999) 17(8): 804-807.

Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.

Xiao et al., "Single-Cell in Situ RNA Analysis With Switchable Fluorescent Oligonucleotides," Front Cell Dev Biol. (2018) 6:42.

Bibikova et al., "Quantitative gene expression profiling in formalin-fixed, paraffin-embedded tissues using universal bead arrays," Am J Pathol. Nov. 2004;165(5):1799-807.

Capodieci et al., "Gene expression profiling in single cells within tissue," Nat Methods. (2005) 2(9): 663-5.

Conze et al., "Single molecule analysis of combinatorial splicing," Nucleic Acids Res. (2010) 38(16): e163.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Hu et al., "A fluorometric lead(II) assay by using a DNA dendrimer as a carrier for the immobilization of the signal probe," Mikrochim Acta. (2019) 186(8):582.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Maierhorfer et al., "Multicolor deconvolution microscopy of thick biological specimens," Am J Pathol. (2003) 162(2): 373-9.

Meade et al. "Multiplexed DNA detection using spectrally encoded porous SiO2 photonic crystal particles," Anal Chem. (2009) 81(7): 2618-25.

Song et al., "Ultrasensitive detection of nucleic acids by template enhanced hybridization followed by rolling circle amplification and catalytic hairpin assembly." Chem Commun (Camb). (2015) 51(12): 2392-5.

Sun et al., "Composite organic-inorganic nanoparticles as Raman labels for tissue analysis," Nano Lett. (2007) 7(2): 351-6.

Weibrecht et al., "Simultaneous visualization of both signaling cascade activity and end-point gene expression in single cells," PLoS One. (2011) 6(5): e20148.

Wilson et al., "Encoded microcarriers for high-throughput multiplexed detection," Angew Chem Int Ed Engl. (2006) 18;45(37): 6104-17.

Zhao et al., "Advances of multiplex and high throughput biomolecular detection technologies based on encoding microparticles," Sci China Chem. (2011) 54(8):1185.

Chen et al., "Efficient in situ barcode sequencing using padlock probe-based BaristaSeq," Nucleic Acids Res. (2018) 46(4): e22.

Sun et al., "Integrating barcoded neuroanatomy with spatial transcriptional profiling enables identification of gene correlates of projections," Nat Neurosci. (2021) 24(6):873-885.

* cited by examiner

FIG. 2A
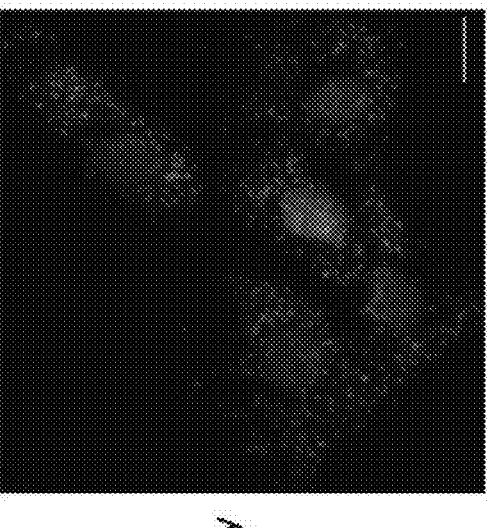
RCA only
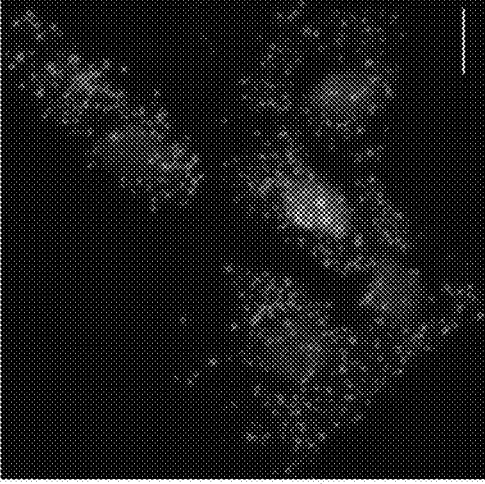
HCR-RCA
FIG. 2B
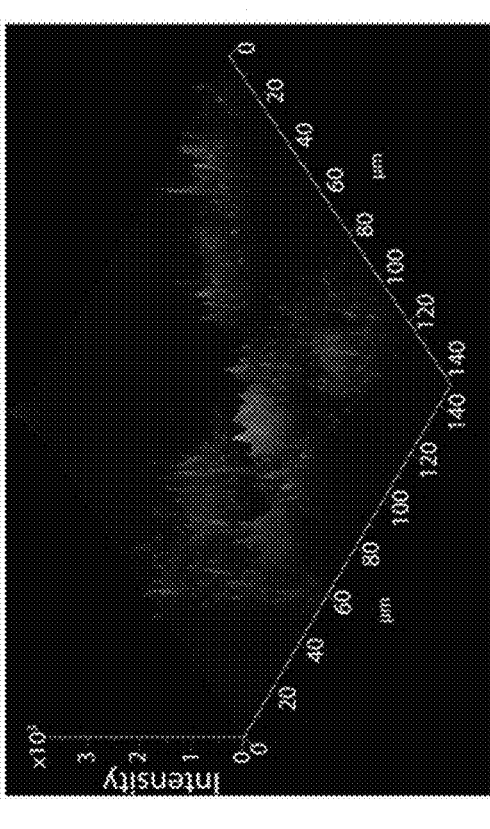

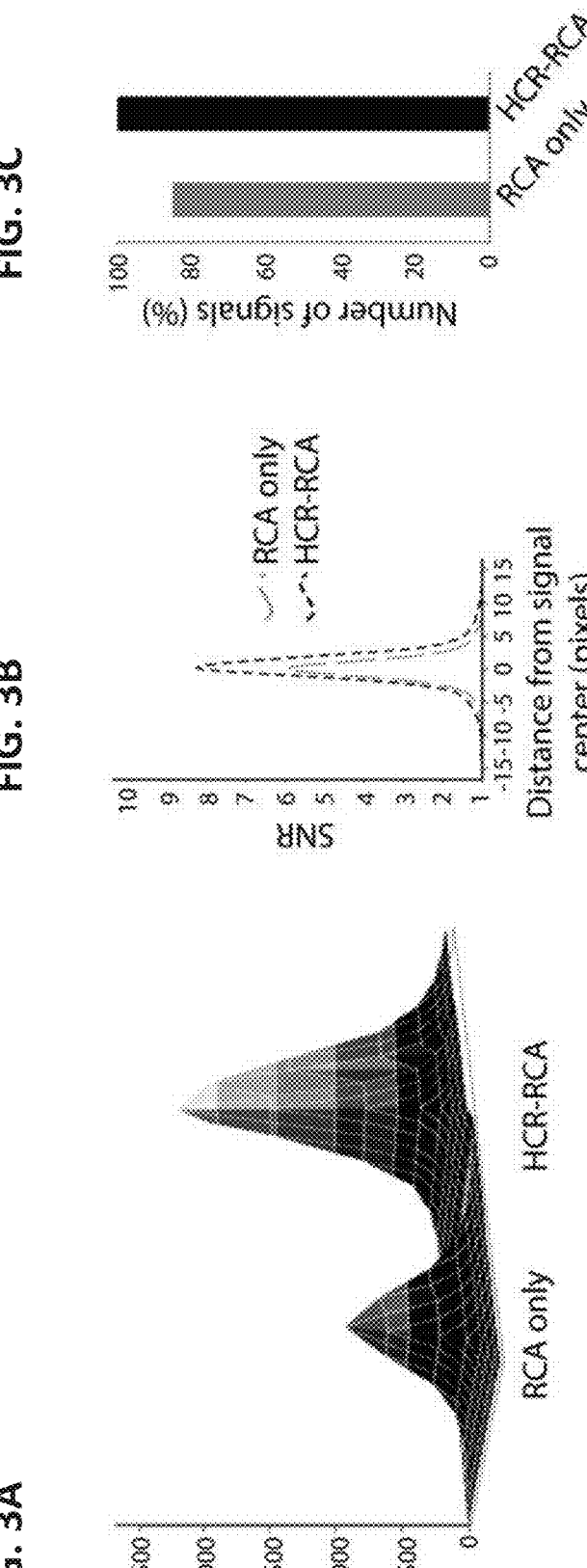

METHOD OF DETECTING AN ANALYTE

CROSS-REFERENCE TO RELATED APPLICATION

This application claims priority to Great Britain Patent Application No. GB1919029.7, filed Dec. 20, 2019, which application is herein incorporated by reference in its entirety for all purposes.

INCORPORATION BY REFERENCE OF SEQUENCE LISTING

The present application is being filed along with a Sequence Listing in electronic format. The Sequence Listing is provided as a file entitled 202412005100SeqList.txt, created Dec. 17, 2020, which is 9,912 bytes in size. The information in the electronic format of the Sequence Listing is incorporated by reference in its entirety.

FIELD

The present disclosure relates to methods and compositions for the detection of target analyte in a sample.

BACKGROUND

Detection of target analyte in a sample, including nucleic acid and non-nucleic acid molecules, are essential for many purposes, such as understanding the molecular basis of cell identity and developing treatment for diseases. Many analyte-detection methods typically involve the detection of fluorescent signals, including particularly for the detection of analytes in situ in the tissues in which they are located. This includes nucleic acids, which it is frequently desirable to detect at the single molecule level. Techniques for quantifying single molecule nucleic acid targets known in the art are generally applicable to tissue samples which have low autofluorescence. However, most human tissue samples, including brain and the vast majority of cancer tissue samples, exhibit high autofluorescence, which makes single molecule quantification difficult. Therefore, there is a need for new and improved methods for the detection of target analyte in a sample.

SUMMARY

Provided herein in some aspects are methods, compositions, devices, and systems for the detection of target analyte in a sample, involving the detection of a nucleic acid or other target analyte by detecting the product of a rolling circle amplification reaction (RCP) which is generated from the analyte or as a reporter for the analyte. The RCP is detected by a hybridisation chain reaction (HCR) reaction performed on the RCP.

In some embodiments, the present disclosure provides a method for detecting a target analyte in a sample, wherein said analyte is a nucleic acid or non-nucleic acid molecule, wherein a rolling circle amplification product (RCP) is provided, wherein said RCP has been generated either from a nucleic acid analyte or as a reporter for an analyte, and comprises multiple repeat copies of a marker sequence indicative of said analyte, and the method comprises (i) performing a hybridisation chain reaction (HCR), wherein said HCR reaction is initiated by an HCR initiator which directly or indirectly hybridises to said marker sequence or which is comprised in said marker sequence; and (ii) detecting the product of the HCR reaction, thereby detecting the target analyte. In some embodiments, the method further comprises a step of providing the RCP.

In any of the preceding embodiments, the target analyte can be a nucleic acid molecule, a lipid or a protein. In some embodiments, the nucleic acid molecule is DNA or RNA, including gDNA, cDNA, mRNA, miRNA, lnRNA or a nucleic acid probe or component of a probe, or an amplification product thereof.

In any of the preceding embodiments, the sample can comprise cells. In some embodiments, the cells are immobilized, fixed or in suspension.

In any of the preceding embodiments, the target analyte can be detected in situ in a tissue sample.

In any of the preceding embodiments, the analyte can be detected in single cells.

In any of the preceding embodiments, a padlock probe comprising a complement of the marker sequence can be hybridized to the target analyte, and can be circularized to form a RCA template, which is subjected to RCA to form the RCP.

In any of the preceding embodiments, the method can be used to detect multiple target analytes in a sample, and at least one RCP can be provided for each target analyte.

In any of the preceding embodiments, HCR can be performed using HCR monomers in the form of hairpins. In some embodiments, the HCR monomers comprise first HCR monomers and second HCR monomers, wherein the first HCR monomers comprise a toehold region which is complementary to the HCR initiator and to the interacting region in the second HCR monomers, and the toehold region in the second HCR monomers is complementary to the interacting region in the first HCR monomers.

In any of the preceding embodiments, the HCR initiator can be provided separately to the RCP and comprises a marker-binding domain capable of hybridising to the marker sequence in the RCP, and wherein the HCR initiator is hybridised to the RCP before the HCR reaction is performed.

In any of the preceding embodiments, at least a fraction of at least one of the HCR monomers in an HCR reaction can be labelled with a detectable label. In some embodiments, the detectable label is a fluorescent label.

In any of the preceding embodiments, for each RCP multiple sequential HCR reactions can be performed, and the respective HCR products may be detected together to provide for detection of the analyte. In some embodiments, sequential HCR reactions are performed using differentially labelled HCR monomer sets, such that each RCP is combinatorially labelled to detect the analyte.

In any of the preceding embodiments, for detecting multiple analytes in sample, a RCP can be provided for each analyte, and said method can be performed sequentially in cycles and a different set of RCPs may be detected in each cycle, to detect a different set of analytes.

In any of the preceding embodiments, in a first cycle, a first set of RCPs can be detected using a first set of HCR initiators each specific for a different member of the first set of RCPs and the HCR products may be removed after the detection, and in a second or subsequent cycle, a second or subsequent set of RCPs can be detected using a second or subsequent set of HCR initiators each specific for a different member of the first or subsequent set of RCPs, and the HCR products may be removed after the detection. In some embodiments, in each cycle the same sets of HCR monomers are used.

In any of the preceding embodiments, the marker sequence can be between about 5 and about 50 nucleotides in length.

In any of the preceding embodiments, the marker sequence can be a barcode sequence between about 8 and about 20 nucleotides in length.

In some embodiments, the present disclosure provides a kit for detecting a nucleic acid or non-nucleic acid target analyte in a sample, said kit comprising: (i) a circular or circularisable probe for detecting a target analyte, and/or a reporter for the target analyte which is or comprises a circular or circularisable nucleic acid molecule, wherein the probe or circular or circularisable nucleic molecule comprises a marker sequence indicative of said analyte; and (ii) means for performing an HCR reaction comprising at least HCR monomers capable of being hybridised together to form an HCR product. In some embodiments, said kit further comprises: (iii) means for performing a RCA reaction; and/or (iv) an HCR initiator.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2B show a representative comparison of signals after RCA only or after HCR-RCA, and corresponding intensity profiles of signals.

FIGS. 3A-3C show a representative comparison of signals between RCA only and HCR-RCA after local background subtraction.

DETAILED DESCRIPTION

Figure 1:
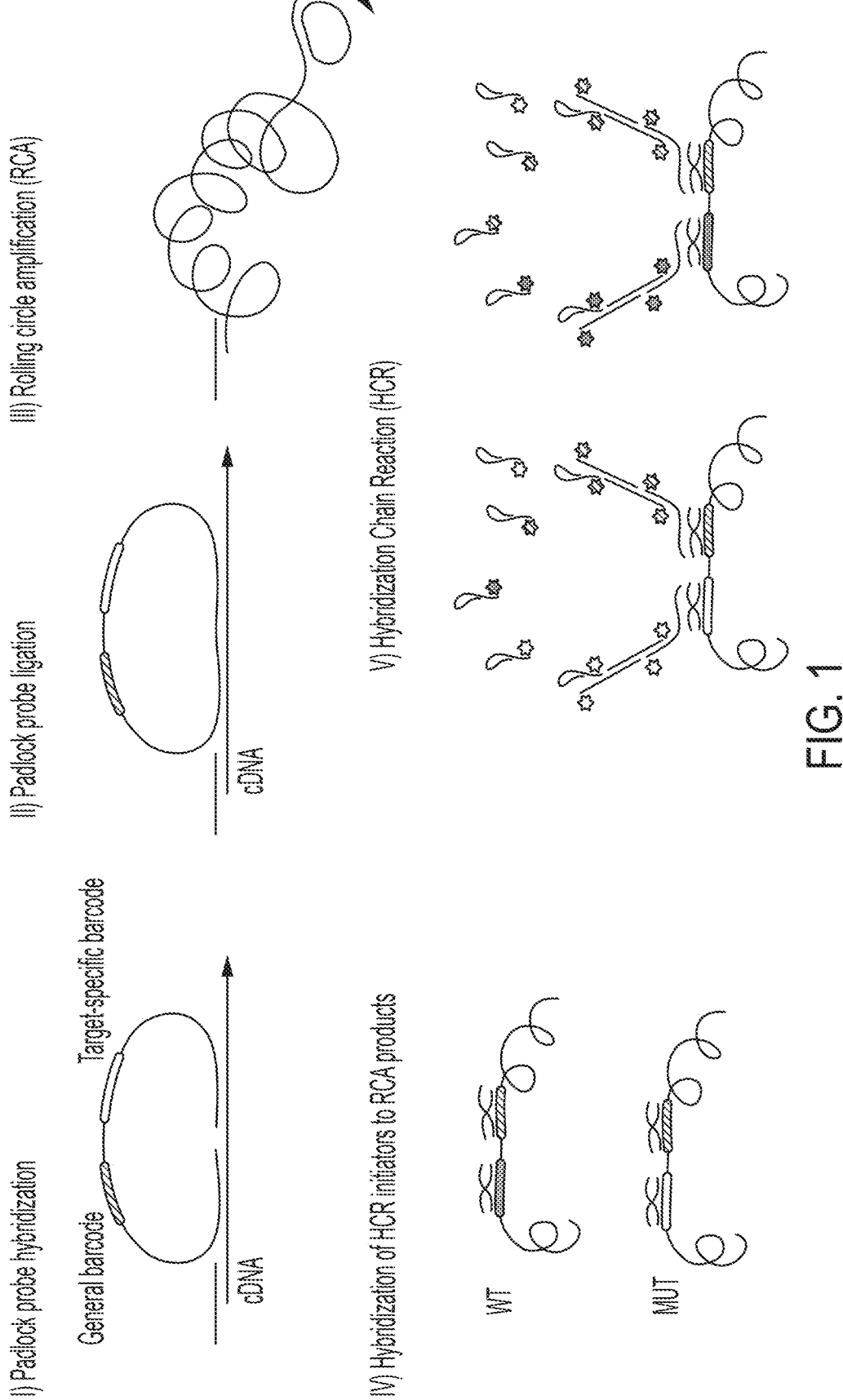
FIG. 1 shows a schematic overview of the RCA-HCR method using padlock probes and RCA.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

The present invention relates to the detection of a target analyte in a sample by a method comprising rolling circle amplification (RCA) and hybridisation chain reaction (HCR). More particularly, the method, termed herein "RCA-HCR", involves detecting a nucleic acid or other target analyte by detecting the product of a rolling circle amplification reaction (RCP) which is generated from the analyte or as a reporter for the analyte. The RCP is detected by an HCR reaction performed on the RCP. HCR is used further to amplify the signal from the RCP, resulting in an improved, more sensitive and specific, method.

Many analyte-detection methods typically involve the detection of fluorescent signals, including particularly for the detection of analytes in situ in the tissues in which they are located. This includes nucleic acids, which it is frequently desirable to detect at the single molecule level. Techniques for quantifying single molecule nucleic acid targets known in the art are generally applicable to tissue samples which have low autofluorescence. However, most human tissue samples, including brain and the vast majority of cancer tissue samples, exhibit high autofluorescence, which makes single molecule quantification difficult.

Single molecule fluorescent in situ hybridization (smFISH) is a widely used technique to determine expression levels by detecting mRNA. In smFISH, a set of typically 30-50 oligonucleotides, each about 20 nucleotides in length and each directly conjugated to a single fluorophore, are first hybridized to a complementary mRNA target. Individual transcripts are then visualized as diffraction-limited spots using wide-field epifluorescence microscopy, and quantified (Raj et al, 2008, Nat Methods, 5, 877-879). Alternatively, smFISH probes may carry, instead of a directly conjugated fluorescent label, a 10-30 nucleotide long overhang sequence, which is not hybridised to the mRNA target, and that can be detected by hybridization thereto of fluorescently conjugated detection probes.

The smFISH technique has been used to quantify the expression and topographic distribution of two prominent breast cancer biomarkers and drug targets, epidermal growth factor receptor 2 (HER2) and estrogen receptor 1 (ER) in formalin-fixed, paraffin-embedded (FFPE) tissue samples. In another study, smFISH was used on mouse brain sections to quantify gene expression of cell type specific marker genes. In order to analyse several marker genes in the same tissue section, smFISH was performed sequentially by first adding a set of smFISH probes for 3 genes, each labelled with a different fluorescent reporter, and then fluorescently imaging the smFISH signals, removing the smFISH probes or the fluorescent labels and then hybridizing a different set of smFISH probes or probe labels for 3 other genes and imaging the smFISH signals. A major limitation of this approach, however, is that the smFISH signals are dim while background fluorescence is high in FFPE samples (with large variability depending on the tissue type, sample age, and fixation conditions).

Hence, imaging at high magnification (60×-100×) is required. As a result, only a very small area of the sample is usually imaged (typically, 40-50 fields of view), thus limiting the ability to detect target analyte variability across a sample. This presents a disadvantage for analysis in cases where there can be a heterogeneity in the presence of the target analyte between different cells or regions of the tissue, for example in tumours, where it is becoming apparent that most cancer types harbour a high degree of intra-tumour heterogeneity and that the spatial distribution of cells expressing a biomarker might also represent a prognostic or predictive factor. It is therefore desirable to develop methods which are able not only to quantitatively determine the expression of a target analyte in a sample, and therefore provide a measure of its abundance, but which can also reflect the spatial distribution and heterogeneity of the target analyte inside the sample.

In order to enable faster imaging, and to improve detection efficiency and specificity in autofluorescent tissues, the signals from fluorescent probes need to be further amplified. For signal amplification, a hybridization chain reaction (HCR) is a very useful technique that allows digital quantification of individual nucleic acid molecules with a detection sensitivity comparable to other methods, and with increased imaging throughput. HCR has previously been combined with smFISH and tissue clearing to increase signal to noise ratio (SNR) in mouse brain samples (Shah et al 2016, Neuron. 92(2):342-357. doi:10.1016/j.neuron.2016.10.001).

RCA has also previously been used as a method of signal amplification in a number of different contexts, including in the detection of nucleic acids in situ in tissue samples. RCA generates a long single stranded concatemeric nucleic acid product composed of multiple tandem repeats that are complementary copies of the circular nucleic acid molecule which is used as the RCA template and thus has been widely used as an amplification strategy for the detection of circular probes or reporter molecules or probes that can be circularised, such as padlock or molecular inversion probes or such like.

Such RCA products (RCPs) may subsequently be labelled by hybridization of hundreds of fluorescently tagged oligonucleotides, generating a strong, locally-enhanced fluorescent signal that can, in some cases, exceed the tissue autofluorescence and therefore enable imaging with lower magnification (20×) and higher speed. However, even RCA assays are limited when applying the assays to tissues with high autofluorescence.

One way to circumvent this problem is quenching of autofluorescence by chemical or fluorescent bleaching. Alternatively, a multitude of tissue clearing techniques have been devised in the recent decade that remove most of the biological content from the tissue sample that is responsible for autofluorescence (lipids and membranes, and protein aggregations). However, many of these tissue clearing procedures are cumbersome, lead to the loss of molecules of interest and may distort the natural morphology of the tissue.

Accordingly, there remains a need for an improved technique for detecting a target analyte in a sample which is capable of providing a signal to noise ratio sufficient to allow fast and precise in situ single molecule imaging.

The present inventors propose a molecular mechanism to address the problem of detecting analytes in autofluorescent samples, by combining the signal amplification power of RCA with that of HCR, further to amplify the signal provided by the RCA reaction. The RCA product (RCP) provides a localised amplified signal to detect the analyte, and this is further amplified by generating and detecting an HCR amplification product which is localised to the RCP. The HCR product in effect becomes a "label" or "signal" for the RCP, which is detected to detect the RCP, which in turn is a reporter for the target analyte. Each monomer repeat of the RCP concatemer may lead to the generation of an HCR signal, resulting in multiple HCR products per RCP. In this way, single molecule detection events may be amplified. The method is capable of providing unprecedented signal to noise ratios even in highly autofluorescent tissue samples. Although of particular benefit for the localised detection of single nucleic acid molecules in tissue samples, including notably RNA, the method is of more general applicability, and provides an improved method of detecting, in any sample, any analyte molecule which may be detected by an assay involving the generation of a RCP, i.e. any assay which uses a circular or circularisable probe or reporter molecule.

In some aspects, the present disclosure, and the present invention, provides a method for detecting a target analyte in a sample, wherein said analyte is a nucleic acid or non-nucleic acid molecule, said method comprising: (i) providing a rolling circle amplification product (RCP), wherein said RCP has been generated either from a nucleic acid analyte or as a reporter for an analyte, and comprises multiple repeat copies of a marker sequence indicative of said analyte; (ii) performing a hybridisation chain reaction (HCR), wherein said HCR reaction is initiated by an HCR initiator which hybridises to said marker sequence or which is comprised in said marker sequence; (iii) detecting the product of the HCR reaction, thereby to detect the target analyte.

In a further aspect, there is provided a kit for detecting a nucleic acid or non-nucleic acid target analyte in a sample, said kit comprising: a circular or circularisable probe for detecting a target analyte, and/or a reporter for the target analyte which is or comprises a circular or circularisable nucleic acid molecule, wherein the probe or circular or circularisable nucleic molecule comprises a marker sequence, or a complement thereof, indicative of said analyte; and means for performing an HCR reaction comprising at least HCR monomers capable of being hybridised together to form an HCR product.

The kit may optionally further comprise: means for performing a RCA reaction, e.g. a polymerase enzyme with strand displacing activity, e.g. Phi29 polymerase and/or a RCA primer; and/or an HCR initiator which is capable of hybridising to said marker sequence or complement thereof.

In the HCR reaction, HCR monomers are polymerised to form an HCR product (HCR polymer) by hybridisation to one another. In particular, a set of HCR monomers designed to hybridise to one another (for example a set of first and second HCR monomers) are polymerised to form an HCR product. The initiator binds to a first HCR monomer, leading it to bind to second HCR monomer, which in turn binds to another first HCR monomer, and so on in a cascade reaction. This is described further below. HCR monomers designed to hybridise to one another to form an HCR product may be termed as "cognate" HCR monomers or as an HCR monomer set, or HCR monomer system. HCR monomers generally have or include a hairpin structure and may alternatively be termed "HCR hairpins" or "monomer hairpins". More generally, HCR monomers may have a metastable secondary structure, as discussed further below. An HCR monomer set may be specific to, or cognate for, a particular HCR initiator sequence, such that for that set the HCR reaction may be triggered (or initiated) only by a particular HCR initiator. The initiator is provided in the marker sequence in the RCP, or may hybridise to the marker sequence in the RCP, and hence the initiation of the HCR reaction is dependent on the presence of the RCP, and is determined by the marker sequence that is present in the RCP.

In an embodiment, the HCR monomers for the HCR reaction may be selected or designed so as to generate an HCR product which is distinctive, or indicative, for the analyte. In an embodiment, the HCR product generated for a given analyte may thus be distinguished from an HCR product generated for another analyte. In another embodiment, multiple HCR products may be generated based on the RCP for a given analyte, and together the multiple HCR products may provide the signal by means of which an analyte is detected and distinguished. For example multiple HCR products may be generated in a combinatorial or sequential labelling scheme, as described further below. Thus, for a given analyte, multiple sets of HCR monomers may be provided, each for a separate HCR reaction. (Each set may comprise the monomers necessary for producing an HCR product, e.g. comprising 2 species of HCR monomers cognate for one another, that is which hybridise together to form an HCR product, and different sets may produce distinct, or distinguishable, HCR products). Alternatively or additionally, multiple sets of HCR monomers may be provided for multiplex detection of multiple different analytes, wherein for each analyte a different set, or different sets, of HCR monomers are provided.

The target analyte to be detected by the methods herein may be any analyte which it is desired to detect. It may thus be any substance, molecule or entity it is desired to detect. The method herein relies upon the generation of a RCP in order to detect the analyte. The RCP is generated by RCA of a circular RCA template molecule, that is a circular nucleic acid molecule. The RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, i.e. where the signal is provided by generating a RCP from a circular RCA template which is provided or generated in the assay, and the RCP is detected to detect the analyte. The RCP may thus be regarded as the ultimate reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularised) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

The term "reporter" is thus used broadly herein to denote a molecule which is used to report on the presence or absence of the analyte—it is a molecule which is detected in the assay method in order to detect the analyte, or which is used or generated as part of the signal generating system to detect the analyte. In the present methods, the reporter is a nucleic acid molecule which is detected as a marker (or proxy or indicator) of the presence of the analyte.

The analyte is the ultimate target of the detection method and may accordingly be any biomolecule or chemical compound, including a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularisable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may thus include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g. through generation of a standard curve). Alternatively, relative quantification can be accomplished by comparison of detected levels or amounts between two or more different target analytes to provide a relative quantification of each of the two or more different analytes, i.e., relative to each other.

In one embodiment the method may be for the localised detection of target analyte. "Localised" detection means that the signal giving rise to the detection of the analyte is localised to the analyte, in this case the RCP and the HCR product are localised to the target analyte. The analyte may therefore be detected in or at its location in the sample. In other words the spatial position (or localization) of the analyte within the sample may be determined (or "detected"). This means that the analyte may be localised to, or within, the cell in which it is expressed, or to a position within a cell or tissue sample. Thus "localised detection" may include determining, measuring, assessing or assaying the presence or amount and location, or absence, of the analyte in any way.

More particularly, the method may be used for the in situ detection of an analyte. In a particular embodiment, the method may be used for the localised, particularly in situ, detection of nucleic acids, particularly mRNA. More particularly, the method may be used for the localised, particularly in situ, detection of mRNA in a sample of cells.

As used herein, the term "in situ" refers to the detection of a target analyte in its native context, i.e. in the cell or tissue in which it normally occurs. Thus, this may refer to the natural or native localization of a target analyte. In other words, the analyte may be detected where, or as, it occurs in its native environment or situation. Thus, the analyte is not moved from its normal location, i.e. it is not isolated or purified in any way, or transferred to another location or medium etc. Typically, this term refers to the analyte as it occurs within a cell or within a cell or tissue sample, e.g. its native localization within the cell or tissue and/or within its normal or native cellular environment. In particular, in situ detection includes detecting the target analyte within a tissue sample, and particularly a tissue section. In other embodiments the method can be carried out on a sample of isolated cells, such that the cells themselves are not in situ.

In other embodiments, the detection is not localized, or not in situ. In other words, the method includes embodiments in which the target analyst is not present (e.g. is not fixed) in its native context. This may include embodiments in which a target analyte is immobilized, e.g. on a solid support. In still other embodiments, the method can be carried out in solution or in suspension. In particular the analyte can be in solution. Thus, for example, the method can be performed on a sample comprising an isolated analyte. In another embodiment the method can be performed where the analyte is suspended in a sample, for example where the analyte is a cell, or an aggregate etc. In still another embodiment, the analyte may be present in or on a cell which is in suspension in the sample, or which is immobilized in the sample etc.

The analyte is present within a sample. The sample may be any sample which contains any amount of target analyte which is to be detected, from any source or of any origin. A sample may thus be any clinical or non-clinical sample, and may be any biological, clinical or environmental sample in which the target analyte may occur. All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared for use in the method of the present invention, or they may be prior-treated in any convenient way e.g. for storage.

As noted above, in one embodiment, the target analyte may be detected in situ, as it naturally occurs in the sample. In such an embodiment the target analyte may be present in a sample at a fixed, detectable or visualisable position in the sample. The sample will thus be any sample which reflects the normal or native ("in situ") localisation of the target analyte, i.e. any sample in which it normally or natively occurs. Such a sample will advantageously be a cell or tissue sample. Particularly preferred are samples such as cultured or harvested or biopsied cell or tissue samples in which the target analyte may be detected to reveal the localisation of the target analyte relative to other features of the sample. In some embodiments, the sample may be a cell or tissue sample possessing a high autofluorescence, in particular a human tissue sample. In some embodiments, the sample may be a cancer tissue sample.

As well as cell or tissue preparations, such samples may also include, for example, dehydrated or fixed biological fluids, and nuclear material such as chromosome/chromatin preparations, e.g. on microscope slides. The samples may be freshly prepared or they may be prior-treated in any convenient way such as by fixation or freezing. Accordingly, fresh, frozen or fixed cells or tissues may be used, e.g. FFPE tissue (Formalin Fixed Paraffin Embedded). Analytes, including cells, or cells which carry or contain an analyte, may be immobilised on a solid support or surface, e.g. a slide, well or beads or other particles etc., using techniques and reagents well known the art, e.g. capture probes and such like, or by chemical bonding or cross-linking etc.

Thus, representative samples may include any material which may contain a target analyte, including for example foods and allied products, clinical and environmental samples, etc. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include clinical samples, e.g. whole blood and blood-derived products such as plasma, serum and buffy coat, blood cells, other circulating cells (e.g. circulating tumour cells), urine, faeces, cerebrospinal fluid or any other body fluids (e.g. respiratory secretions, saliva, milk, etc.), tissues, biopsies, as well as other samples such as cell cultures, cell suspensions, conditioned media or other samples of cell culture constituents, etc. The sample may be pre-treated in any convenient or desired way to prepare for use in the methods of the present invention, for example by cell lysis or purification, fixing of cells, isolation of the analyte, immobilisation etc.

Although the method of the present invention may be used to select a target analyte in an in situ (i.e. a native) setting, it is also contemplated that the method may be employed to select a target analyte in any detection system, including where a target analyte has been isolated or purified from its native setting. The sample may thus be a direct product of a target analyte isolation procedure, or of a cell lysis procedure, or it may further be fractionated or purified in some way. Thus, the analyte may be a synthetic molecule such as a cDNA or an amplicon etc., and the sample may be any material or medium containing such a molecule, e.g. a reaction mixture.

According to the method of the present invention, a rolling circle amplification product is provided which has been generated from a target analyte or as a reporter for said analyte, and which comprises multiple repeat copies of a marker sequence indicative of said analyte. The marker sequence is in turn involved in the initiation of the HCR reaction, the product of which is ultimately detected in order to indicate the presence of the target analyte. The marker sequence for a given target analyte must therefore be specific to that analyte, or unique, such that multiple target analytes can be distinguished from each other.

A "marker sequence" is thus a sequence which marks or identifies a given analyte. It a sequence by which a given analyte may be detected and distinguished from other analytes. Where an "analyte" comprises a group of related molecules e.g. isoforms or variants or mutants etc., or molecules in a particular class or group, it is not required that a marker is unique or specific to only one particular analyte molecule, and it may be used to denote or identify the analyte as a group. However, where desired, a marker sequence may be unique or specific to a particular specific analyte molecule, e.g. a particular variant. In this way different variants, or isoforms, or mutants may be identified or distinguished from one another.

Where the target analyte is a nucleic acid molecule the marker sequence may be a sequence present in the analyte molecule, or a complement thereof (e.g. a reverse complement thereof). It may therefore be or comprise a variant or mutant sequence etc. present in the analyte, or a conserved sequence present in an analyte group which is specific to that group. The marker sequence may alternatively be incorporated into the RCP as a tag or identifier (ID) sequence (e.g. a barcode) for the analyte (including for a nucleic acid analyte). It may thus be a synthetic or artificial sequence.

The marker sequence may thus be a complementary copy of a sequence present in the RCA template which is used to generate the RCP. The marker complement sequence may be provided in the RCA template as a tag or identifier sequence for the analyte, for example where the RCA template is or is generated from a probe (e.g. a circularisable probe such as a padlock probe), or where the RCA template is a reporter for the analyte (e.g. in an immunoRCA reaction). It will be understood in this regard that the sequence in the RCA template which is complementary to the marker sequence present in the RCP may itself be regarded as a marker sequence. The RCA template may be provided or generated from a probe or reporter molecule which is designed to detect a particular analyte, and thus such a probe or reporter molecule may be viewed as comprising a marker sequence for that analyte—the marker sequence is then copied, as a complementary sequence, into the RCP. The term "marker sequence" can therefore encompass both a marker sequence present in the RCP and its complement (more particularly reverse complement) present in the RCA template. Accordingly, a "marker sequence" can include the complementary sequence.

In some embodiments, where the target analyte is a nucleic acid molecule, the target analyte molecule itself which is present in the sample may be directly incorporated into the RCA template—in other words a target nucleic acid molecule, or a fragment thereof, may be circularised to form the RCA template. A marker sequence (specifically a marker complement sequence) present in the target analyte may thus be incorporated into the RCA template. Such a method may involve capture of a target nucleic acid fragment and circularisation, e.g. by ligation on a template. Probes are known in the art which may be used to capture and template the ligation of captured target nucleic acid molecules. Such circularisation adaptors include the so-called "Selector" probes of WO 2003/012119, WO 2005/111236, WO 2005/070630 and EP 1997909. Such probes have target binding regions designed to bind to the two respective ends of target nucleic acid fragments to bring them into juxtaposition for ligation together, directly or indirectly, to form a circular molecule of, or containing, the target nucleic acid fragment. A circularised Selector probe may contain the target nucleic acid analyte and a Selector probe sequence, for example where the Selector is a partially double-stranded construct comprising a long strand with single-stranded target-complementary end regions which hybridise to the respective ends of the target molecule and bring them into juxtaposition for ligation to the respective ends of the shorter strand of the Selector probe. As an alternative to using a marker sequence present in the analyte nucleic acid, a marker sequence may be contained in the shorter strand of the Selector probe which becomes ligated to the target molecule. Such probes are used to capture nucleic acid fragments and hence are not applicable to detection of nucleic acids in situ. Generally, a step of preparing fragments containing the target nucleic acid molecule is required.

Other types of probe may be used to generate circular molecules comprising a complementary copy of a target nucleic acid sequence, for example gap-filling padlock probes, or molecular inversion probes and such like. Such probes are well known and widely used and described in the art. Alternatively, as described further below padlock probes may be used to detect target nucleic acids without generating a complementary copy of the target nucleic acid, wherein simply hybridisation and ligation of the padlock probe on the target nucleic acid is detected. All such probes may be used to detect nucleic acids in situ. The target nucleic acid, or a complementary copy thereof may be used to prime the RCA of the circularised probe, and thereby localise the RCP to the target nucleic acid, thereby enabling a localised detection.

As is clear from the above, the target analyte may be any nucleic acid molecule, including DNA, RNA, or a mixture thereof. Moreover, the target analyte may be any form of nucleic acid, such as mRNA, cDNA, etc. The sample may undergo any necessary treatments to prepare the target analyte for detection. In some embodiments, the RNA present in the sample may be reverse transcribed into cDNA, for example by contacting the sample with a reverse transcriptase enzyme and appropriate primers. Such enzymes and primers are well known in the art, and any suitable enzymes and primers may be employed. This reverse transcription reaction may be carried out in situ, following fixing of cells in the sample. In such an embodiment, the cDNA produced by the reverse transcription reaction can then be considered as the target analyte to be detected.

As is further clear from the above discussion, circularisable probes, or indeed more generally circularisable reporter molecules, may be used to generate the RCA template which is used to generate the RCP. By "circularisable" is meant that the probe or reporter (the RCA template) is in the form of a linear molecule having ligatable ends which may circularised by ligating the ends together directly or indirectly, i.e. to each other, or to the respective ends of an intervening ("gap") oligonucleotide or to an extended 3' end of the circularisable RCA template. A circularisable template may also be provided in two or more parts, namely two or more molecules (i.e. oligonucleotides) which may be ligated together to form a circle. When said RCA template is circularisable it is circularised by ligation prior to RCA. Ligation may be templated using a ligation template, and in the case of padlock and molecular inversion probes and such like the target analyte may provide the ligation template, or it may be separately provided. The circularisable RCA template (or template part or portion) will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

In the case of padlock probes, in one embodiment the ends of the padlock probe may be brought into proximity to each other by hybridisation to adjacent sequences on a target nucleic acid molecule (such as a target analyte), which acts as a ligation template, thus allowing the ends to be ligated together to form a circular nucleic acid molecule, allowing the circularised padlock probe to act as a template for an RCA reaction. In such an example the terminal sequences of the padlock probe which hybridise to the target nucleic acid molecule will be specific to the target analyte in question, and will be replicated repeatedly in the RCP. They may therefore act as a marker sequence indicative of that target analyte. Accordingly, it can be seen that the marker sequence in the RCP may be equivalent to a sequence present in the target analyte itself. Alternatively, a marker sequence (e.g. tag or barcode sequence) may be provided in the non-target complementary parts of the padlock probe. In still a further embodiment, the marker sequence may be present in the gap oligonucleotide which is hybridised between the respective hybridised ends of the padlock probe, where they are hybridised to non-adjacent sequences in the target molecule. Such gap-filling padlock probes are akin to molecular inversion probes.

Accordingly, similar circular RCA template molecules can be generated using molecular inversion probes. Like padlock probes, these are also typically linear nucleic acid molecules capable of hybridising to a target nucleic acid molecule (such as a target analyte) and being circularised. The two ends of the molecular inversion probe may hybridise to the target nucleic acid molecule at sites which are proximate but not directly adjacent to each other, resulting in a gap between the two ends. The size of this gap may range from only a single nucleotide in some embodiments, to larger gaps of 100 to 500 nucleotides, or longer, in other embodiments. Accordingly, it is necessary to supply a polymerase and a source of nucleotides, or an additional gap-filling oligonucleotide, in order to fill the gap between the two ends of the molecular inversion probe, such that it can be circularised.

As with the padlock probe, the terminal sequences of the molecular inversion probe which hybridise to the target nucleic acid molecule, and the sequence between them, will be specific to the target analyte in question, and will be replicated repeatedly in the RCP. They may therefore act as a marker sequence indicative of that target analyte. Alternatively, a marker sequence (e.g. tag or barcode sequence) may be provided in the non-target complementary parts of the molecular inversion probe.

Other types of probe which result in circular molecules which can be detected by RCA and which comprise either a target analyte sequence or a complement thereof have been developed by Olink Bioscience (now Navinci Diagnostics AB) and include the Selector-type probes described in WO 2016/016450, which comprise sequences capable of directing the cleavage of a target nucleic acid molecule (i.e. a target analyte) so as to release a fragment comprising a target sequence from the target analyte and sequences capable of templating the circularisation and ligation of the fragment. WO 2016/016452 describes probes which comprise a 3' sequence capable of hybridising to a target nucleic acid molecule (i.e. a target analyte) and acting as a primer for the production of a complement of a target sequence within the target nucleic acid molecule (i.e. by target templated extension of the primer), and an internal sequence capable of templating the circularisation and ligation of the extended probe comprising the reverse complement of the target sequence within the target analyte and a portion of the probe. In the case of both such probes, target sequences or complements thereof are incorporated into a circularised molecule which acts as the template for the RCA reaction to generate the RCP, which consequently comprises concatenated repeats of said target sequence. Again, said target sequence may act as, or may comprise a marker sequence within the RCP indicative of the target analyte in question. Alternatively, a marker sequence (e.g. tag or barcode sequence) may be provided in the non-target complementary parts of the probes.

As noted above, in some embodiments the present method may use an RCP which has been generated as a reporter for the target analyte. In such embodiments, the RCA reactions may amplify a circular nucleic acid molecule (RCA template) which is a reporter for the presence of the target analyte. Such a RCA template may contain a marker sequence (or more particularly a complement thereof), in order to produce an RCP comprising multiple repeat copies of a marker sequence indicative of said target analyte. In this case, the method may be used for the detection of any target analyte, including a nucleic acid molecule, or an analyte other than a nucleic acid molecule, such as a protein, peptide etc. In such embodiments, the marker sequence is a sequence other than a sequence that is present in the target analyte itself. The marker sequence may be present in a probe molecule (such as padlock or molecular inversion probe, or any other probe described or mentioned above), or it may be present in a circular or circularisable nucleic acid reporter molecule which is used in conjunction with a probe to detect the target analyte.

A variety of assays have been developed wherein a nucleic acid molecule (e.g. probe or reporter molecule) may be used to directly or indirectly tag or "label" a target analyte in a sample. In such embodiments, this may be a circular or circularisable nucleic acid molecule, which may provide a template for an RCA reaction, thereby effecting the generation of an RCP as a reporter for the target analyte. The marker sequence present in such an RCP, which is indicative of said target analyte, may thus be a complementary copy of a sequence present in the probe. This marker sequence will be associated with the target analyte via the probe or reporter, when the probe is bound to the analyte, and if necessary when the probe or reporter is circularised, such that detection of the RCP, indirectly via detection of the product of the subsequent HCR reaction, serves to indicate the presence of the target analyte in the sample.

In some methods, a new nucleic acid molecule may be generated in a sample (i.e. a nucleic acid molecule that was not present in the original sample and was not one of the components added to the sample) by one or more molecules that interact with, e.g. bind to, the target analyte. The detection of the generated nucleic acid molecule is indicative of the target analyte in a sample. The generated molecule may be a circular molecule, or it may template the circularisation of another molecule, such as a padlock probe for the generated molecule.

Various methods based upon detecting such a proxy or marker nucleic acid molecule using an RCA reaction as part of the detection strategy, i.e. for generating an RCP indicative of the target analyte, are well described in the art, including, for example, immunoRCA, assays using padlock probes and proximity probe assays which generate a circular nucleic acid molecule. In all these cases, the methods rely on providing or generating a circular nucleic acid molecule which may then be used as a substrate (template) for an RCA reaction, and the RCA product may then be detected as a reporter for the analyte, i.e. as a substitute for detecting the target analyte directly.

ImmunoRCA typically uses a conjugate comprising an antibody specific for a target analyte linked to an oligonucleotide, although any binding partner specific for the analyte may be used. The target analyte is contacted with the antibody:oligonucleotide conjugate. A circular or circularisable oligonucleotide (such as a padlock probe or similar, for example), is hybridized to the oligonucleotide conjugated to the antibody (the circular/circularisable oligonucleotide may be pre-hybridized or added after the antibody has been allowed to interact with the target analyte). The sample is then subjected to an RCA reaction to amplify the circular/ circularised oligonucleotide. The circular or circularisable oligonucleotide provide as the RCA template in an immunoRCA method may comprise a marker sequence. In this way, the resulting RCP comprises multiple repeat copies of the marker sequence.

This method also has the advantage that the oligonucleotide conjugated to the antibody is used as the primer for the RCA reaction. As a result of this arrangement, the RCA product is tethered to the antibody that is interacting with the target analyte, thereby allowing localised detection of the analyte in the sample. This is particularly useful in in situ applications, e.g. in a cell or tissue sample, where information about the location of different target analytes within the cell or tissue can be obtained.

Analogously to immunoRCA, hybridisation probes may be used to detect nucleic acid analytes, which are provided with, or designed to hybridise to, circular RCA templates or circularisable RCA template molecules, e.g. FISH and smFISH assays in which the hybridisation probes comprise, in addition to a target-specific binding domain for hybridisation to a target molecule, a second domain, which does not hybridise to the target nucleic acid but which contains a binding site for a circular or circularisable probe, which may, upon circularisation if necessary, be subjected to RCA. Such hybridisation probes may be provided as hairpins which open upon binding of the probe to its target, releasing the second domain for hybridisation to the circular or circularisable probe.

Proximity assays may also be designed for use with an RCA-based detection system, wherein a circular nucleic acid molecule is generated as a result of the interaction of the interaction of the nucleic acid domains of proximity probes with each other, or with added oligonucleotides. In a proximity assay a target analyte is detected by the binding of multiple (i.e. two or more, generally two or three) probes which, when brought into proximity to each other by binding to the target analyte (hence "proximity probes"), allow a signal to be generated. Typically, the proximity probes each comprise a nucleic acid domain linked to the target-analyte-binding domain of the probe, and generation of the signal involves an interaction between the nucleic acid moieties. Thus, signal generation is dependent on an interaction between the nucleic acid moieties and hence only occurs when the probes have both (or all) bound to the target analyte, thereby lending improved specificity to the detection system. For example, proximity ligation assays (PLAs) rely on proximal binding of proximity probes to an analyte to generate a signal from a ligation reaction involving or mediated by (e.g. between and/or templated by) the nucleic acid domains of the proximity probes. Such a ligation reaction may result in the generation of a circular nucleic acid molecule. Proximity extension assays (PEAs) may generate an extended nucleic acid molecule wherein the nucleic acid domain of one proximity probe is extended using the nucleic acid domain of another proximity probe as extension template. The extended molecule may be detected by hybridisation of a circular or circularisable oligonucleotide which acts as a RCA template for a RCA reaction.

The nucleic acid domains of the proximity probes when in proximity may template the ligation of one or more added oligonucleotides to each other, including an intramolecular ligation, to circularise one or more added linear oligonucleotides, to form a nucleic acid circle, based on the padlock probe principle, as described, for example, by Landegren et al. in WO 99/49079. In such a method, the ends of the added linear oligonucleotide(s) are brought into juxtaposition for ligation by hybridising to one or more circularisation templates provided by the nucleic acid domain of one or more proximity probes. Various such assay formats are described in WO 01/61037.

It will accordingly be evident that the RCP that is provided in the method of the present invention may be used to detect any target analyte in a sample, regardless of whether it has been generated from the target analyte, i.e. from the "original" nucleic acid molecule in a sample, where the target analyte is a nucleic acid; or whether it is generated as a reporter for the target analyte, and is derived from a "proxy" nucleic acid molecule provided in the assay, or generated, for example by the interaction of specific detection molecules, e.g. immunoRCA or proximity probes, with the target analyte, e.g. where the target analyte is a protein.

Alternatively put, the RCP that is provided in the method of the present invention may be any RCP which can be generated in the course of a detection assay. The use of a proxy nucleic acid molecule to generate the RCP is necessary where the target analyte is not a nucleic acid molecule, such as where the target analyte is a protein or a peptide, but may also be implemented where the target analyte is a nucleic acid molecule.

Since the RCP may be generated according to known assay methods, the performance of steps of the method leading to the generation or provision of the RCP will thus generally be according to methods and principles well known and understood in the art. Thus, a sample containing the analyte may be incubated with probes, to allow the probes to bind or interact with the analyte, e.g. to hybridise to a nucleic acid analyte, or for antibody-based probes to bind to the analyte. Conditions for such an incubation step are known in the art, and may be varied according to the sample, or analyte, or probes used, etc. This may include washing steps to remove unbound probes etc. Where necessary, this may be followed by a reaction to circularise a circularisable probe or reporter molecule, again according to well-known procedures. Ligation reactions for circularisation of such probes or reporter molecules are also well known and described in the art, and a variety of different template-directed ligases may be used, including temperature sensitive and thermostable ligases, such as bacteriophage T4 DNA ligase, bacteriophage T7 ligase, E. coli ligase, Taq ligase, Tth ligase, Ampligase® and Pfu ligase. Certain RNA ligases may also be employed in the methods of the invention. A suitable ligase and any reagents that are necessary and/or desirable may be combined with the sample/reaction mixture and maintained under conditions sufficient for ligation to occur. Ligation reaction conditions are well known in the art and may depend on the ligase enzyme used.

The next step following a ligation step (if required) is to generate the RCP. RCA is well known in the art, and procedures are widely described in the literature. The primer for the RCA will depend on the assay format, and may be provided by a target nucleic acid analyte (e.g. to which a circularisable probe has hybridised), by a probe or a part thereof, e.g. by the conjugated oligonucleotide of an immunoRCA probe or the nucleic acid domain of a proximity probe, or it may be separately provided. A RCA primer will be of sufficient length, to provide for hybridization to the RCA template under annealing conditions.

In addition to the above components, the RCA reaction mixture includes a polymerase, e.g. phi29 polymerase, and other components required for a DNA polymerase reaction. The desired polymerase activity may be provided by one or more distinct polymerase enzymes. In some embodiments the polymerase has exonuclease activity, e.g. 5' and/or 3' exonuclease activity. 3' exonuclease activity may be desirable, in order to digest the 3' end of a probe or target molecule to generate a hybridised 3' end (to the RCA template) which can act as a primer for the RCA reaction.

In preparing the reaction mixture of this step of the subject methods, the various constituent components may be combined in any convenient order. For example, all of the various constituent components may be combined at the same time to produce the reaction mixture.

Regardless of the mechanism by which is the RCA template is provided or generated, the RCP that is provided in the method herein comprises multiple repeat (tandem) copies of a marker sequence which is indicative of the target analyte. The marker sequence is used in the initiation of the HCR reaction, either directly as an HCR initiator (i.e. the marker sequence is or comprises as sequence which functions as an HCR initiator) or as binding site for a separately-provided HCR initiator. Since the RCP is a concatemer of monomer repeats, multiple HCR initiators or HCR initiator binding sites are provided. Thus, where a separate HCR initiator is used, the method comprises hybridising a multiplicity of HCR initiators to the RCP, or more particularly to the marker sequences present in the repeats (monomer units) thereof. As used herein the term "multiple" or "multiplicity" means two or more, e.g. at least 2, 3, 4, 5, 6, 10, 20, 30, 50, 70 or 100 or more. It will be understood that whilst each of the repeat units or monomers of RCP comprise the binding site for the HCR initiator, in practice not all of these binding sites may (or will) be occupied by an initiator after initiator hybridisation. It suffices that a number, or multiplicity, of such binding sites are bound by an initiator. Thus, in the method the initiator hybridises to a marker sequence in at least one monomer of the RCP, but preferably to multiple marker sequences.

In any of the preceding embodiments, the marker sequence can be between about 5 and about 10, about 10 and about 15, about 15 and about 20, about 20 and about 25, about 25 and about 30, about 30 and about 35, about 35 and about 40, about 40 and about 45, or about 45 and about 50 nucleotides in length. In any of the preceding embodiments, the marker sequence can be a barcode sequence between about 8 and about 20 nucleotides in length, e.g., between about 10 and about 16 nucleotides in length, The method relies upon multiple HCR initiators or HCR monomers being able to hybridise to the RCP. Accordingly, it will be understood that the RCP needs to be available for such hybridisation. This requirement is a feature of all RCA-based detection methods, where an RCA product is detected by hybridising a probe, e.g. a detection probe, to the product, and is well understood in the art. Thus, it may be advantageous for the RCP to have low secondary structure. However, this feature may be compensated for by performing the method in conditions which favour hybridisation, according to principles well known in the art. Thus, for example, the method can be performed in the presence of formamide e.g. in buffers containing formamide.

HCR is a well-known technique for enzyme-free nucleic acid amplification based on a triggered chain of hybridisation of nucleic acid molecules starting from HCR monomers, which hybridise to one another to form a nicked nucleic acid polymer. This polymer is the product of the HCR reaction which is ultimately detected in order to indicate the presence of the target analyte.

HCR is described in detail in Dirks and Pierce, 2004, PNAS, 101(43), 15275-15278 and in U.S. Pat. Nos. 7,632, 641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401).

HCR monomers typically comprise a hairpin, or other metastable nucleic acid structure. In the simplest form of HCR, two different types of stable hairpin monomer, referred to here as first and second HCR monomers, undergo a chain reaction of hybridisation events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridisation to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), i.e. a sequence which is complementary to the exposed toehold region (input domain) of the first HCR monomers. Crucially, however, in the absence of the HCR initiator, these interacting regions are protected by the secondary structure (i.e. they are not exposed), and thus the hairpin monomers are stable or kinetically trapped (also referred to as "metastable"), and remain as monomers (i.e. preventing the system from rapidly equilibrating), because the first and second sets of HCR monomers cannot hybridise to each other. However, once the initiator is introduced, it is able to hybridise to the exposed toehold region of a first HCR monomer, and invade it, causing it to open up. This exposes the interacting region of the first HCR monomer (i.e. the sequence of complementarity to the toehold region of the second HCR monomers), allowing it to hybridise to and invade a second HCR monomer at the toehold region. This hybridisation and invasion in turn opens up the second HCR monomer, exposing its interacting region (which is complementary to the toehold region of the first HCR monomers), and allowing it to hybridise to and invade another first HCR monomer. The reaction continues in this manner until all of the HCR monomers are exhausted (i.e. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridisation to and invasion of a first HCR monomer. The first and second HCR monomers are designed to hybridise to one another are thus may be defined as cognate to one another. They are also cognate to a given HCR initiator sequence. HCR monomers which interact with one another (hybridise) may be described as a set of HCR monomers or an HCR monomer, or hairpin, system.

It can be seen that the HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerisation reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described, and may be used in the methods herein.

A fundamental principle behind HCR is that short loops of nucleic acid are resistant to invasion by complementary single stranded nucleic acids. This stability allows for the storage of potential energy in the form of nucleic acid loops. Potential energy is released when a triggered conformational change allows the single stranded bases which were present in the loops to hybridise with a complementary strand. HCR monomers may thus contain such a loop, as well as a region of complementarity to another HCR monomer which is shielded or protected by the loop structure, such that it can only hybridise to the other HCR monomer when the loop structure is opened up. In a conventional system involving a set of two species of HCR monomers, the first HCR monomers each have a toehold region which is complementary to the interacting region present in each of the second HCR monomers. Similarly, each monomer in the second HCR monomers has a toehold region which is complementary to the interacting region present in each of the first HCR monomers. Accordingly, the HCR reaction proceeds with individual HCR monomers from alternating species of monomer being invaded, opening so as to expose their interacting region, and hybridising via said interacting region to the toehold region of an HCR monomer of the opposing or cognate species.

The HCR monomers may contain a region of self-complementarity. The self-complementary regions may hybridise to one another to form a region of secondary structure. In some embodiments, the region of secondary structure will contain a loop of single stranded nucleic acid, more particularly a stem-loop or hairpin structure comprising a double stranded "stem" region and a single stranded loop. More particularly, the secondary structure may be a metastable secondary structure. In preferred embodiments, the metastable secondary structure is or comprises a stem-loop, or hairpin.

"Metastable", as used herein, means that the HCR monomer is kinetically disfavoured from associating with another molecule with which it is designed to associate (specifically, hybridise), such as another HCR monomer, in the absence of an initiator or activator for the reaction or interaction, i.e. an HCR initiator. The HCR monomers are thus kinetically trapped, that is, they retain their secondary structure; they are stable in the absence of an initiator, and the system as a whole is therefore is unable to equilibrate. Thus, the HCR reaction relies on changes in secondary structure induced in a metastable secondary structure by an HCR initiator. When the initiator sequence is contacted with the HCR monomers, it can hybridise to the toehold region of a first HCR monomer via its toehold binding region, and thereby disrupt (e.g. invade) the secondary structure of that HCR monomer.

The interacting region of the HCR monomers is contained in the secondary structure in order to protect it from interacting with other HCR monomers in the absence of the HCR initiator, i.e. until said secondary structure is disrupted by hybridisation and invasion at the toehold region. To effect this protection, the interacting region may be present in the loop region of the HCR monomers, or alternatively in the stem region of the HCR monomers.

The single stranded toehold region of the HCR monomers is also involved in triggering the HCR reaction. When the initiator is introduced, it hybridises to the toehold region of a first HCR monomer and invades the secondary structure, displacing the intramolecular interactions responsible for the metastable structure, thereby opening it up and triggering a chain reaction of alternating kinetic escapes (loop structure openings) by the two monomer species, allowing them to hybridise and thereby corresponding to "polymerisation" into a nicked double stranded polymer.

Where the HCR initiator is a sequence comprised in the marker sequence of the RCP, the toehold region of the first HCR monomer may hybridise to it, and this hybridisation may cause the metastable structure of the first HCR monomer to open. In other words, the marker sequence comprises a sequence complementary to at least part of the toehold sequence of a first HCR monomer, (and thus acts as a toehold binding region). The marker sequence may contain a further sequence complementary to a sequence within the secondary structure of the first HCR monomer (e.g. within the stem sequence which follows the toehold), and hence once the toehold has bound, strand displacement may occur to open the metastable secondary structure and allow the further sequence to bind.

In the case where the HCR initiator is a separate molecule comprising a sequence capable of hybridising to the marker sequence, the HCR initiator may comprise a region of complementarity to the marker sequence, that is a marker-binding sequence, i.e. an RCP binding region or domain (or more particularly a marker sequence binding-domain), and a second domain, which does not bind to the RCP and which contains a sequence complementary to a sequence within the accessible toehold region of a first HCR monomer i.e. a toehold binding region or domain. Such a sequence is the sequence which initiates the HCR reaction and may be termed the "initiator sequence", or initiator domain.

The initiator may in some embodiments initially be "protected" or shielded from being able to hybridise to the first HCR monomer and thereby initiate an HCR reaction before hybridisation to the RCP. This protection or shielding of the HCR initiator may be provided in the form of a metastable secondary structure (more particularly a double stranded metastable secondary structure, e.g. a stem-loop structure akin to that of an HCR monomer). Interaction of the initiator with the marker sequence of the RCP, for example, can cause the metastable secondary structure to be disrupted, or unfolded (namely "opened up"), thereby exposing the HCR initiator which is then free to hybridise to the first HCR monomer and set off, or trigger, the HCR reaction.

Various HCR initiator designs have been proposed, which may include metastable hairpin structures as described above, and/or which comprise "bridge" molecules, wherein the actual initiator sequence is hybridised to a pair of bridge molecules which each hybridise to the target nucleic acid molecule (which in this case would be the RCP), or wherein the initiator is "split" and provided in two parts, which each hybridise to their target molecule (here the RCP), in order to together provide a complete HCR initiator. See for example the designs HCR v2.0 and HCR v3.0 described by Choi et al., 2018, Development 145(12) dev165753. Any such initiator designs may be used in the method. Accordingly, where a separately provided HCR initiator molecule is used, it may be provided in one or more parts, e.g. two or more parts, e.g. 1, 2 or 3 parts.

In order to prevent premature initiation of the HCR reaction, or initiation of the HCR reaction in a location independent of the RCP, where the HCR initiator is a sequence capable of hybridising to the marker sequence in the RCP, it may be hybridised to the RCP before the HCR monomers are added. As the RCP comprises multiple repeat copies of the marker sequence, it can be seen that a number of copies of the HCR initiator can be hybridised to a single RCP, for example, with at least one HCR initiator hybridised to the RCP at each repeat of the marker sequence. As will be discussed in more detail below, it may be that more than one HCR initiator is capable of binding to the RCP at each monomer repeat within the RCP, including at a site other than the marker sequence, as well as within the marker sequence in each repeat.

In some embodiments, the method of the present invention may comprise a step of washing the RCP once it has been contacted with the HCR initiator, so as to remove any unhybridised HCR initiators. This washing step may be conducted by contacting the RCP with any suitable buffer, as known in the art.

Once the HCR initiators have been hybridised to the marker sequences in the RCP, and any unhybridised initiator sequences have been washed away, the HCR monomers may be introduced. This ensures that the HCR reactions are localised to the RCP. Depending on the method by which the RCP is provided, it may be the case that the RCP in turn is localised to the target analyte. In such cases, the HCR reaction is then effectively localised to the target analyte, and thus detection of the product of the HCR reaction provides information not only about the presence of the target analyte, but also about its location. This is particularly important in applications where a target analyte is to be detected in situ, i.e. in the location where it would typically exist within the sample.

Accordingly, in some embodiments, the HCR reaction of the method involves contacting the RCP with a plurality of HCR initiators, such that said HCR initiators can hybridise to the repeat copies of the marker sequence of the RCP. Following the hybridisation of the HCR initiators to the RCP, and an optional step of washing the RCP to remove unhybridised initiators, the reaction may comprise contacting the RCP to which the HCR initiators have been hybridised with at least one set of HCR monomers.

In some embodiments, the HCR reaction may comprise contacting an RCP comprising multiple repeat copies of a marker sequence capable of acting as an HCR initiator with at least one set of HCR monomers.

The metastable secondary structure of the HCR monomers may comprise at least one loop, more particularly a single stranded nucleic acid loop, and at least one double-stranded region, more particularly a region of self-complementarity wherein two self-complementary regions or portions of the HCR monomer hybridise together, e.g. to form a stem or stem-like structure. Thus in an embodiment the metastable secondary structure is (e.g. consists of) or comprises a stem-loop or hairpin.

In many embodiments, the secondary structure will be, or will comprise, a single stem-loop or hairpin structure. However, as is known in the art, other secondary structures can be designed and envisaged. Thus for example the secondary structure can contain two or more loops, e.g. two loops. For example, a hairpin structure may be modified to include a second loop in one "strand" of the stem—one of the self-complementary regions which hybridise to form the stem of the hairpin may contain a stretch of non-complementary nucleotides, that is nucleotides which are not complementary and hence do not hybridise to the other self-complementary region which make up the stem, and which consequently "bulge" out to form a loop (a so-called "bulge-loop"). A hairpin structure may also be modified to include regions of mismatch between the two strands of the stem. In another embodiment, two hairpin structures may be connected by a single-stranded region. Such secondary structures are commonly used in the design of HCR monomers designed to achieve greater than linear HCR amplification (see e.g. U.S. Pat. No. 7,721,721, particularly FIGS. 3 and 4 thereof).

In addition to the HCR reaction discussed above, which is initiated by an HCR initiator hybridising to or contained within the marker sequence in the RCP, the present method may further comprise performing a second HCR reaction, which is not analyte-specific. This may act as a positive control. Such a further HCR reaction may thus be a general, or control, reaction. This reaction is unrelated to the identity of the target analyte, but may be used to confirm that an RCP has been generated, and/or may be useful in multiplex situations or where sequential labelling is taking place (e.g. where multiple HCR products are sequentially generated for each analyte or marker sequence), and/or in the analysis of the results, e.g. where the HCR products are detected by imaging, to align images etc. This control or general HCR reaction may be initiated via a general (e.g. common or control) sequence present in the RCP. This functions in a manner akin or analogous to the marker sequence but is not analyte-specific. Thus, the general sequence is separate to the marker sequence and may be present in the RCP that is generated for all analytes (in other words it may be a sequence that is common to the RCP provided for any analyte). Accordingly a separate general HCR initiator may be used, and this may be provided by a separate general HCR initiator molecule, which hybridises to the general sequence in the RCP or, alternatively, general HCR initiator sequence may be present within the general sequence present within the RCP. The general HCR reaction also involves of a separate set of HCR monomers, which ensures that the resulting HCR product can be distinguished from any target-specific HCR products. The separate general and target-specific HCR reactions may be conducted simultaneously, or sequentially, i.e. the general HCR reaction may be conducted at the same time as, before or after the target-specific HCR reaction.

The method may be carried out in multiplex to detect different target analytes in a given sample. Alternatively put, the method of the present invention may be used to detect multiple (i.e. 2 or more) target analytes in a given sample.

In certain embodiments a sample may be assayed for two or more different target analytes. In such embodiments, at least one RCP is provided for each target analyte, i.e. multiple RCPs may be used. In this respect, the methods of the invention are particularly advantageous for the detection of multiple analytes in a sample. For high (or higher) multiplex, a sequential method may be carried out, in which a number of analytes are detected using multiple initiators and/or HCR monomer sets, one per analyte in a first cycle of the method, and in subsequent cycles, different analytes are detected using the same HCR monomer sets (optionally with initiators having the same initiator sequence as in the first cycle). Thus, the same monomer sets may be used in different cycles of the method, to detect different analytes. For example, for the first cycle, the HCR initiators may each comprise a marker-binding sequence (marker-binding domain) specific for a different target analyte to be detected or assayed in the first cycle. Each HCR initiator used in the cycle may comprise an initiator sequence which is different from other initiators used in the cycle, and is designed to initiate HCR of a different HCR monomer set. In a second or subsequent cycle, the HCR initiators may each have a different marker-binding sequence (to each other, and to the HCR initiators used in the first cycle, or in other cycles), but may have an initiator sequence common to that used in a previous or other cycle, but for each cycle the multiple HCR initiators will each be different, with a different initiator sequence. In such a sequential method, the HCR products may be stripped, or removed, from the sample, between cycles (e.g. after each cycle) for example as described in more detail below There is no restriction on the type of target analytes that may be detected in multiplex. Accordingly, the method may be applied in multiplex to detect multiple nucleic acid target analytes, or multiple non-nucleic acid target analytes, or a mixture of nucleic acid and non-nucleic acid target analytes. In order for multiple target analytes to be distinguished from each other, the RCPs that are provided in respect of each target analyte must have different marker sequences, i.e. each target analyte must be associated with a specific, distinct marker sequence. Similarly, the specific marker sequences for each target analyte in a run of the method (e.g. in a cycle of the method, or for each analyte to be detected or assayed in a sample at the same time), may in turn hybridise to separate and distinct HCR initiator sequences, such that each target analyte is also associated with a specific, distinct (e.g. unique) HCR initiator sequence, in order to initiate the polymerisation of a specific arrangement of HCR monomers, and therefore the production of a specific HCR product which may be distinguished from other HCR products. The number of different target analytes that can be detected in a given sample is therefore limited only by the ability of the detection methods available to distinguish between different HCR products, which indicate different marker sequences and therefore different target analytes.

Further, in some embodiments, multiple RCPs may be provided for each analyte, and these may be detected commonly as a group (i.e. they may share a common marker sequence, or in other words have the same marker sequence) or they may be detected individually (i.e. they may each have a different marker sequence). This may be of interest, for example in the detection of a nucleic acid molecule, e.g. RNA, in a manner akin to smFISH, where multiple probes are used, each hybridising to a different target sequence in the target analyte. The probes may each provide or lead to the generation of a RCA template, and hence to a separate RCP.

Accordingly, for multiplex methods, where more than one RCP is generated, they may be distinguished from one another on the basis of the HCR products generated, and this may be achieved in various ways. The marker sequence in each RCP may be distinct, and may lead to the generation of a distinct HCR product, which may be distinguished from other HCR products. However, multiplexing capacity may be limited by the number of available labels or detection systems for the HCR products. To increase multiplexing capacity sequential visualisation or labelling strategies may be used. The generation of an HCR product may be viewed as the generation of a "label" or "signal" for the RCP, and hence multiple HCR products may be sequentially generated for each RCP, to achieve sequential "HCR labelling". Each HCR reaction may be separated by, e.g. stripping or bleaching steps to remove the preceding HCR product, or the signal therefrom. Methods of sequential visualisation reactions which may be adapted for use in the present methods are known in the art, e.g. Göransson et al., 2009 (A single molecule array for digital targeted molecular analyses. Nucleic Acids Res. 2009 January; 37(1):e7), Wahlby et al., 2002 (Sequential immunofluorescence staining and image analysis for detection of large numbers of antigens in individual cell nuclei. Cytometry, 47(1):32-41, 2002).

Combinatorial methods of labelling, e.g. ratio labelling, using different combinations and/or ratios of different labels are known in the art and may be used to increase the number of different RCPs and hence different analytes which may detected at one time, or in the same reaction. For example, combinations using different coloured and/or fluorescent labels and/or different ratios of different coloured and/or fluorescent labels may be used. For example, such "colour"-coding with different combinations of coloured and/or fluorescent labels may be used in multiplex assays based on detection by flow cytometry or microscopy (e.g. by imaging). Alternatively, using lanthanide isotope labels cyToF detection may be used. By way of example, 7 different fluorophores may be grouped into 4 different types. There are 7 different combinations if labelled with only one colour, with 2 colours there are 21 different combinations, for 3 and 4 colours there are 35 different combinations and so on.

Such methods may therefore rely on generating a sequence of HCR products which may be detected to generate a sequence of signals, by means of which a RCP, and hence an analyte may be detected. In other words, each analyte is detected and distinguished by a combinatorial signal, or more particularly a combinatorial HCR "labelling" scheme. Such a sequential combinatorial labelling scheme is demonstrated in Example 1 below.

In some representative embodiments of the invention, multiple analytes may be detected in parallel. For example for a given sample, multiple analytes may be detected at the same time, e.g. in the same reaction. In other representative embodiments of the invention, multiple analytes may be detected sequentially.

A combinatorial detection method may involve using a set of HCR initiator molecules for each marker sequence in a RCP, which are used sequentially, with a cognate set of HCR monomers for each HCR initiator, and an HCR signal is detected for each HCR reaction in sequence, together to provide the distinguishing signal for that marker sequence (and hence RCP). Thus whilst different HCR monomer sets may be provided with or detected by the same label, the particular combination and sequence of labels detected will identify and distinguish the particular initiator set/marker sequence. By way of example, in a first cycle, a first HCR initiator may be used which is cognate for an HCR monomer set detectable by a first label. The first HCR product may be detected, and it may then be removed from the RCP. In the second cycle a second HCR initiator may be used, having the same binding domain as the first HCR initiator but a different second domain which hybridises to the first HCR monomer of a second HCR monomer set which is detectable by a second label, and so on in subsequent cycles, to build up a "label sequence". The number of cycles may vary depending on the degree of multiplexing required, e.g. 2, 3, 4, 5, 6, or more cycles. It will be understood that it is not necessary for each cycle to have a different label, and the same label could be used in different cycles (but not in all of the cycles); what is required is that for each marker sequence a different sequence of labels is determined.

Thus the same marker sequence may support the generation of multiple sequential HCR products, which may be detected in sequence, together to provide a signal which identifies and distinguishes that marker sequence, and hence the RCP and/or analyte.

In such sequential labelling methods, the marker sequence present in the RCP may be considered as a single continuous sequence, in the sense that it provides a single binding site for an HCR initiator. However, as a variation to this approach the marker sequence may be arranged in the form of a barcode sequence with multiple separate barcode positions which are "read" separately and sequentially, in order to detect and identify the marker sequence. In such a scheme an HCR product may be generated and detected for each barcode position, in sequence. This may be performed by a sequential HCR labelling method similar to the above, except that for each barcode sequence a set of HCR initiators will be provided which each has a different binding domain, each specific for a different barcode position.

In the present method, the step of performing an HCR reaction in order to generate a detectable HCR product may therefore comprise multiple individual HCR reactions. Accordingly, it may be seen that in different ways a single marker sequence may be capable of supporting (or initiating) multiple HCR reactions. Analogously to the above, if the HCR initiator is contained within the marker sequence in the RCP, then the marker sequence may comprise multiple adjacent or sequential HCR initiator sequences, each capable of hybridising to a different HCR monomer and therefore of initiating an independent HCR reaction.

To perform sequential HCR labelling reactions it may be desirable or in some cases necessary to remove a detected HCR product, before the next cycle is performed (i.e. before the next sequential HCR reaction is initiated). There are a number of methods by which this can be done, which are known in the art. Such methods may include the use of high temperature and/or chemical agents, such as formamide, to denature or disrupt the hybrid between the RCP and the HCR initiator or first HCR monomer. However, in some cases it may be desirable to use less harsh methods and displacement probes may be used, for example invading probes, which invade the hybrid between the RCP (marker sequence) and the HCR initiator or first HCR monomer, in order to displace the hybridised HCR product. Various such displacement (or displacer) probes have been described, for example the so-called "eraser probes" of Xiao and Guo 2018, Front Cell Dev Biol 6:42, doi 103389/fcell 2018.00042 and Douse et al 2012, NAR 40(7) 3289-3298, which may adapted for use herein. This may include providing the HCR initiator with a separate displacer-binding toehold domain, which does not hybridise to the RCP nor to an HCR initiator, and which is available for binding to a displacer probe.

In some embodiments, the first and/or second HCR monomers may comprise an overhang region (i.e. a displacer-binding toehold domain) capable of facilitating a displacement reaction to depolymerise the HCR product. This overhang region may be targeted by displacement probes. Such displacement probes comprise a sequence complementary to the overhang region, and may further comprise a sequence complementary to at least a portion of the input/output domain of the first or second HCR monomer. Accordingly, they can hybridise to the overhang region of the HCR monomers within the HCR product, with the overhang region acting as a toehold, and invade the hybrid between the first and second monomers in the polymeric HCR product, thus leading to the dissociation of the HCR product. This displacement-initiated depolymerisation method may be particularly useful in situations where the method involves the use of an HCR initiator complex capable of supporting multiple HCR reactions. In such situations, the HCR products may be too large to be effectively removed from the target nucleic acid molecule without the use of high temperatures and/or harsh chemical agents, which may damage the sample. Accordingly, breaking up the polymeric chain allows for the HCR product to be more readily removed. In some embodiments, this displacement mechanism may be combined with the use of temperature/chemical agents, as discussed above, in order to facilitate the removal of the HCR product.

In some situations, toehold-mediated displacement may not be necessary in order to displace a preceding HCR product. For example, it may be sufficient to simply rely on equilibrium kinetics, wherein unbound preceding HCR initiators and/or HCR monomers are washed away, and subsequent HCR initiator and/or HCR monomers are added in excess, such that the signal from the subsequent HCR product can be detected at sufficient strength.

Any appropriate mechanism for removing previous HCR products once they have been detected in order to allow subsequent HCR reactions to proceed may be implemented in the present method. Following the step of dehybridising the preceding HCR products, it may be advantageous to also include a step of washing the sample so as to remove the previous HCR products from the sample.

The HCR product may be detected using any convenient protocol. The particular detection protocol may vary depending on the sensitivity desired and the application in which the method is being practiced. The polymer HCR product may be detected in a number of different ways. Any method known for the detection of nucleic acids may be used, for example based on size separation, e.g. various forms of electrophoresis, nucleic acid staining techniques, light scattering spectroscopy, such as dynamic light scattering (DLS), viscosity measurement, mass changes determined by e.g. surface plasmon resonance and spectrophotometric techniques based on detection of colorimetric or fluorescent labels etc. In this regard, the HCR product may be directly labelled by incorporating a label into it, or it may be indirectly labelled e.g. by hybridising or otherwise binding a labelled detection probe to it. For example, a detection probe may be designed to hybridise to a particular sequence (e.g. a tag sequence, or detection sequence) present in one or more HCR monomers.

Conveniently, one or more of the HCR monomers may be labelled, e.g., fluorescently, or otherwise spectrophotometrically, or radioisotopically labelled or with any detectable label, such that the HCR product itself is directly labelled. In some embodiments, the direct labels may be incorporated into one or both (or more) of the cognate HCR monomers in a set, e.g. either the first HCR monomers, or the second HCR monomers, or all of the HCR monomers may be labelled. If only one of the species of HCR monomers is labelled, the other species of HCR monomers in a set of cognate monomers can act as unlabelled 'linkers', which facilitate the polymerisation of the labelled monomers. The labelled monomers may be seen as "detection HCR monomers" or "detection HCR oligonucleotides".

In an alternative embodiment, only a fraction of one or both or more species of the HCR monomers may be labelled, i.e. it may not be necessary for all of the HCR monomers of a given species to comprise a label. This may be useful where it is desired to reduce the cost involved, as labelled HCR monomers may be more expensive than unlabelled HCR monomers.

Moreover, it is not necessary for all of the HCR monomers within a given set of HCR monomers (e.g. the first and second HCR monomers) to have the same detectable label. Accordingly, in some embodiments, the different HCR monomer species within a given set of HCR monomers may comprise different detectable labels. Alternatively put, there may be multiple different detectable labels present within a given set of HCR monomers. This may be particularly useful in multiplex applications, i.e. when assessing samples containing multiple different target analytes, where it is necessary to distinguish between multiple different HCR products.

Alternatively, the HCR monomers may be labelled, akin to conformationally selective probes such as molecular beacons, such that the signal (e.g. fluorescence) is quenched when the HCR monomers are in monomer form and exhibit a metastable secondary structure, but detectable when the monomers have been unfolded, i.e. when hybridised in the polymer. This may be done by labelling the HCR monomers with energy transfer labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

Thus, for example, the HCR monomers may be labelled at one end of a stem region with a quencher molecule and with a fluorophore at the opposing side of the duplex region, such that when the stem structure is present in the monomer the fluorescent signal is quenched. Upon polymerisation the fluorophore and quencher are spatially separated in the polymer, and the quenching is relieved, allowing a fluorescent signal to be detected. Thus an HCR monomer may be labelled in a conformationally sensitive way. In an alternative embodiment, the acceptor and donor molecules for an energy transfer reaction may be provided on different monomers, which upon unfolding and hybridisation to one another allow a FRET-pair to form, and thus generate signal. In a still further format, the acceptor and donor molecules may be provided as described in e.g., LOCI (U.S. Pat. Nos. 5,340,716; 6,346,384), or as described in U.S. Pat. No. 8,198,031. The presence of an HCR product may therefore be determined via the use of an energy transfer reaction such as FRET.

Various dyes or stains may be used to selectively detect double stranded DNA products, e.g., via intercalation. Accordingly, the double stranded HCR product may be detected using such molecules. Representative detectable molecules include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. Alternatively, the nucleic acid stain may be or may incorporate an acridine dye, or a homo- or heterodimer thereof, such as acridine orange, acridine homodimer, ethidium-acridine heterodimer, or 9-amino-6-chloro-2-methoxyacridin, or an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). The nucleic acid stain may also be a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) may be used, including nucleic acid stains commercially available under the trademarks TOTO® (e.g., quinolinium, 1-1'-[1,3-propanediylbis[(dimethyliminio)-3.1-propanediyl]]bis[4-[(3-methyl-2(3H)-benzothiaz-olylidene)methyl]]-,tetraiodide), BOBO™ (e.g., 2,2'-[1,3-propanediylbis[(dimethyliminio)-3,1-propanediyl-1(4H)-pyridinyl-4-ylidenemethy-lidyne]]bis[3-methyl]-tetraiodide), POPO™ (e.g., benzoxazolium, 2,2'-[1,3-propanediyylbis[(dimethyliminio)-3,1-prpanediyl-1(4H)-pyridinyl-4-ylidenemethylidyne]]bis[3-methly]-, tetraiodide), YOYO™ (stain), TO-PRO™ (e.g., quinolinium, 4-[(3-methyl-2(3H)-benzothiazolylidene) methyl]-1-[3-(trimethylammonio)propyl]-, diiodide), BO-PRO™ (stain), PO-PRO™ (e.g., benzoxazolium, 3-methyl-2-[[1-[3-(trimethylammonio)propyl]-4(1H)-pyrudubylidene]methyl]-diiodide) and YO-PRO™ (e.g., 4-[(3-methyl-2(3H)-benzoxazolylidene)methyl]-1-[3-(trimethylammonio)propyl]-quinolinium diiodide) from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) may be used, including nucleic acid stains commercially available under the trademarks SYBR® Green (stain), EvaGreen® (stain), SYTO™ (stain), SYTOX™ (stain), PICOGREEN™ (stain), OLIGREEN™ (stain), and RIBOGREEN™ (stain) from Molecular Probes, Inc., Eugene, Oreg. In yet other embodiments, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO™ (stain), SYTOX™ (stain), JOJO™ (e.g., 2,2'-{propane-1,3-diylbis[(dimethylammonio)propane-3,1-diylquinolin-1-yl-4-ylidenemethylylidene]}bis(4-methyl[1,3]oxazolo[4,5-b]pyridin-4-ium) tetraiodide), JO-PRO™ (stain), LOLO™ (e.g., 2,2'-{propane-1,3-diylbis[(dimethylammonio)propane-3,1-diylquinolin-1-yl-4-ylidenemethylylidene]}bis(6-bromo-4-methyl[1,3]thiazolo [4,5-b]pyridin-4-ium) tetraiodide), LO-PRO™ (stain) from Molecular Probes, Inc., Eugene, Oreg.

In embodiments in which the detection system is specific for the HCR polymer in question, as opposed to double stranded nucleic acid molecules in general, the detection system may, as noted above, include a detection probe (e.g. a detection oligonucleotide) that specifically binds to a detection sequence found in the HCR product. For example, a detection probe may be designed to hybridise to a particular sequence (e.g. a tag sequence) present in one or more HCR monomers. In some embodiments, both sets of HCR monomers may contain tag sequences, such that all of the HCR monomers present in the final HCR product can be labelled. In an alternative embodiment, only one set of HCR monomers may contain such a tag sequence.

A nucleic acid detection probe will comprise a sequence complementary to that of the tag sequence in the corresponding HCR monomer, such that it can hybridise to, and therefore label, the HCR monomer. The detection probe also comprises a detectable label. This may be either a directly or indirectly detectable label.

In this context, a directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy®3-CTP (cyanine3-CTP), Cy®5-CTP (cyanine5-CTP)) etc. Fluorescent moieties which may be used to tag nucleotides for producing labelled probe nucleic acids include, but are not limited to: fluorescein, the cyanine dyes, such as Cy®3 (cyanine3), Cy®5 (cyanine5), Alexa Fluor® 555 (fluorescent moiety), Bodipy™ 630/650 (fluorescent moiety), and the like. Other labels as are known in the art, such as those described above, may also be employed.

In certain embodiments, as described above, the HCR monomers may be labelled with "energy transfer" labels. As an alternative to labelling the HCR monomer, an energy transfer labelled detection probe e.g., oligonucleotide, may be used. Specific examples of such labelled oligonucleotide probes include the TaqMan® type probes, as described in U.S. Pat. No. 6,248,526, (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Other types of probe structures include: Scorpion probes (as described in Whitcombe et al., Nature Biotechnology (1999) 17:804-807; U.S. Pat. No. 6,326,145), Sunrise probes (as described in Nazarenko et al., Nuc. Acids Res. (1997) 25:2516-2521; U.S. Pat. No. 6,117,635), Molecular Beacons (Tyagi et al., Nature Biotechnology (1996) 14:303-308; U.S. Pat. No. 5,989,823).

The step of detecting the HCR product may comprise detecting a signal from the labelled HCR product. The method of signal detection may vary depending on the particular signal producing system which is employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample or a cell sample on a microscope slide, fluorescence may be detected using a fluorescence microscope. Conveniently, imaging may be used, and e.g. fluorescent microscopic images may be obtained and analysed, as demonstrated in the Example below. Fluorescence may be suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, data may be collected in this way at frequent intervals, for example once every 3 minutes, throughout the reaction. By monitoring the fluorescence of the reactive molecule from the sample the progress of the polymerisation reaction can be monitored in various ways.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other.

The data generated as described above can be interpreted in various ways. For example, simply the presence or absence of analyte may be determined by detecting the polymer. However, since the size of the HCR product is inversely related to the amount of target analyte in a sample, quantitative measurements may be possible. Accordingly, the concentration of analyte may be determined. This may conveniently be done by determining the average molecular weight of the HCR polymer product, which may be done using standard techniques. Standard curves and control samples may be used.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of HCR initiators and/or HCR monomers that may be employed typically ranges from about 2 to about 20 or higher, e.g., as up to 100 or higher, 1000 or higher, etc. wherein the multiple analytes in a sample may be detected in parallel or sequentially.

The method of the invention may be homogenous or heterogeneous. That is, it may be performed in solution, without a solid phase or support (i.e. without immobilisation of any reaction components) or it may be performed in an immobilised or solid phase-based format, for example where the RCP is immobilised. Immobilisation of the RCP may be achieved in various ways. For example in an in situ assay the RCP be formed in a RCA reaction primed using a target (analyte) nucleic acid as the RCA primer. Here the RCP is attached to the target tissue sample which is itself fixed to a solid support. This may occur for example where a target nucleic acid is detected using a padlock probe. In another embodiment, a target analyte may be immobilised, e.g. by use of an immobilised capture probe. Alternatively, the RCA may be primed by a nucleic acid domain of an immunoRCA or a proximity probe, which is bound to an immobilised (or fixed) analyte target. In other embodiments, the primer for the RCA reaction may simply be immobilised to a solid support. Use of a heterogeneous, immobilised format allows washes to be readily performed, and hence for example allows for ready removal of unbound probes, and/or or other unreacted reaction components added, or spurious unwanted reactions, not physically attached to the surface. Thus, a heterogeneous, or solid phase-based method may readily be performed sequentially.

The various nucleic acid reaction components used in the present method, such as probes or reporter molecules for making the RCP, the HCR initiator or HCR monomers, and any detection or displacer probes etc., may be made up of ribonucleotides and/or deoxyribonucleotides as well as synthetic nucleotide residues that are capable of participating in Watson-Crick type or analogous base pair interactions. Thus, the components may be DNA and/or RNA or any modification thereof e.g. PNA or other derivatives containing non-nucleotide backbones. Conveniently they may be DNA.

Several of the reaction components used in the method herein hybridise to one another and accordingly have regions, or domains, of complementarity, which allow hybridisation to take place.

The term "hybridisation" or "hybridises" as used herein refers to the formation of a duplex between nucleotide sequences which are sufficiently complementary to form duplexes via Watson-Crick base pairing or any analogous base pair interactions. Two nucleotide sequences are "complementary" to one another when those molecules share base pair organization homology. Hence, a region or domain of complementarity refers to a region or domain of sequence that is capable of forming an intra- or intermolecular duplex, i.e. either a duplex within the same molecule (e.g. a hairpin structure) or a duplex with a different molecule.

"Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. In the case of the RCP and the RCA template, where the RCP is produced as a complementary copy of the template, the two sequences will generally have complete, or almost complete (depending on enzyme fidelity) complementarity in base sequence. However, for components which are designed to hybridise to one another (e.g. probes, reporter molecules, HCR initiators etc.), two sequences need not have perfect homology to be "complementary", or capable of hybridisation. Usually two sequences are sufficiently complementary when at least about 85% (preferably at least about 90%, and most preferably at least about 95%) of the nucleotides share base pair organization over a defined length of the molecule. The degree of mismatch tolerated can be controlled by suitable adjustment of the hybridisation conditions. Those skilled in the art of nucleic acid technology can determine duplex stability empirically considering a number of variables including, for example, the length and base pair composition of the respective molecules, ionic strength, and incidence of mismatched base pairs, following the guidance provided by the art. Thus the design of appropriate reaction components, and domains thereof, and the conditions under which they hybridise to their respective targets is well within the routine skill of the person skilled in the art.

It will be evident that the present methods of detection may be applied to any scenario where it is desired to detect, quantify and/or locate a target analyte, and particularly a number (i.e. multiplicity) of target analytes. The method may be used, for example, in in situ applications to detect or assess gene expression. In addition, the method may be applied in vitro to distinguish a set of target analytes, such as target nucleic acid molecules, for example following production of a cell extract. The target nucleic acids may be, or may be derived from, target nucleic acid molecules present in any sample under investigation.

The method provides an advantage in terms of the signal amplification afforded by the combination of RCA and HCR, resulting in strong signal intensity. This allows highly sensitive detection of analytes, and enables, for example, the detection of rare transcripts or mutations, including in difficult, e.g. autofluorescent samples. The method allows for fast highly multiplexed detection, particularly when used with a sequential HCR labelling strategy. The method further allows the ability to detect analytes such as mRNA, and hence to image gene expression, over a wide portion of a tissue section at low magnification (e.g. X20 objective) and is applicable to archival FFPE tissue sections and aged FFPE samples in which smFISH and other fluorescence-based detection strategies are notoriously challenging. The method may also have applicability to tissue microarrays for high throughput screening of potentially useful biomarkers. The method therefore has particular applicability for gene expression studies in tissue sample, including single cell studies.

Such features make the method a powerful tool that can be integrated in routine pathological diagnostics, i.e. the method is suited to use in clinical diagnostic laboratories. Furthermore, it may also be a useful research tool, for example to study or quantify expression levels and investigate the spatial distribution of gene expression. This may be of particular use in neuroscience, to chart the spatial morphology of genes in brain samples, or to identify cellular sub-types on the basis of gene expression patterns. The method can be used to identify the spatial location of both lowly expressed and newly predicted cellular subtypes based on the detection of a set of transcripts that specifically marks a given cell subtype due to its specificity. High-throughput spatial transcriptomic techniques, including sequential smFISH, spatial transcriptomics and MERFISH, have also been applied to map cellular diversity in human and mouse brain. However, these methods are technically challenging and still require posterior validation by lower-throughput assays such as smFISH. In this context, the present method could prove very valuable especially when samples characterized by high levels of tissue autofluorescence need to be analysed (e.g., aged brain).

Finally, as the method allows the detection of a strong signal, the method could be applied to detect short RNAs or to discriminate between different splicing variants, which is not possible by smFISH. In summary, the method is a versatile, scalable and cost-effective method that can be used to quantify individual analytes, such as RNA molecules also in challenging FFPE samples, with broad applications ranging from research to routine diagnostics.

II. Terminology

Specific terminology is used throughout this disclosure to explain various aspects of the apparatus, systems, methods, and compositions that are described.

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(ix) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(x) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oNTM DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ Thermo-Script™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actino-mycin D. Many sequence-modified derivative or mutants of reverse transcriptase enzymes, e.g. M-MLV, and compositions including unmodified and modified enzymes are commercially available, e.g. ArrayScript™, MultiScribe™ ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xi) Label, Detectable Label, and Optical Label

The terms "detectable label" and "label" are used interchangeably herein to refer to a directly or indirectly detectable moiety that is associated with (e.g., conjugated to) a molecule to be detected, e.g., a probe for in situ assay, or analyte. The detectable label can be directly detectable by itself (e.g., radioisotope labels or optical labels, such as fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature. For example, detectably labeled features can include a fluorescent, a colorimetric, or a chemiluminescent label attached to an analyte, probe, or bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore.

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethyl-amino and—methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLE

The following example is included for illustrative purposes only and is not intended to limit the scope of the present disclosure.

Example 1: Multiplexable Single Molecule mRNA Detection and Quantification in Tissue Samples

Materials and Methods

Tissues and Cell Lines

The in situ somatic mutation analyses of colon cancer and patient-matched normal tissues were approved by the Regional Ethical Review Board of Uppsala (2007/116). The tumour biopsy material used for targeted sequencing analysis and basic clinicopathological data were anonymously provided by pathologists without any patient identity or related information, and do not require ethical permission, since only research with biological material that can be traced to a person is subject to ethical approval (The Swedish ethical review act; 2003:460, section 4; 3).

Mouse Tissue Section Preparation

Mouse strain C57BL/6 at 30 days age (P30) was euthanized and the olfactory bulb was dissected via cryosectioning. Cryosectioning was performed on ThermoFisher cryostat, at 10 µm thickness. Sections were then adhered onto ThermoFisher Superfrost glass slides and stored at −70 C until processing.

Cell Culture and Sample Preparation

The cell line BJ-hTERT (ATCC CRL-4001) was cultured in DMEM (Gibco) without phenol red and 1-glutamine, supplemented with 10% FBS (Sigma), 2 mM 1-glutamine (Sigma) and 1×PEST (Sigma). The cell line was incubated at 37° C., 5% CO2.

To prepare cell samples, confluent cell lines were treated with 0.25% (w/v) trypsin-EDTA (Sigma) and resuspended in culturing medium. Resuspended cells were then seeded on Superfrost Plus slides (Thermo) placed in a 150 mm×25 mm Petri dish (Corning), and culturing medium was added to a final volume of 25 ml. Three millilitres of resuspended cells were used to seed five slides. Cells were incubated in the same previous conditions 12-24 h before fixation. Slides with cocultured cell lines were prepared as described above with a mixture of different cell lines. Fixation was performed in 3% (w/v) paraformaldehyde (Sigma) in DEPC-treated PBS for 30 min at RT after removal of the culturing medium and two washes in PBS. After fixation, slides were washed twice in DEPC-treated PBS and dehydrated in an ethanol series of 70%, 85% and 100% for 5 min each. All of the following reactions were performed in Secure-Seal hybridization chambers (Invitrogen).

HCR-RCA for Sensitive KRAS Wild Type and Mutation Single Molecule Detection

The RCA part including rolling circle amplified Padlock probes was performed as previously described (Ida Grundberg et al. In situ mutation detection and visualization of intratumor heterogeneity for cancer research and diagnostics. Oncotarget. 2013; 4(12):2407-2418. doi:10.18632/oncotarget.1527). In short, tissues or cells were fixed with 3.7% PFA on Superfrost Plus (ThermoFisher) glass slides followed by reverse transcription of RNA to cDNA (with TranscriptMe, Blirt) in situ using LNA modified primers. KRAS wild type- and mutation-specific as well as ACTB padlock probes were then hybridized to cDNA and perfectly matching padlock probes became ligated (with Ampligase, Genecraft) and could be amplified through rolling circle amplification (RCA) for 3 h (with Phi29, Monserate). To image signals after the RCA part only, RCA products were labelled with fluorescent detection probes that were then stripped off with 65% formamide (Sigma-Aldrich) for 3×30 seconds before HCR was performed. HCR included hybridization of 0.1 µM v.3 HCR-initiator probes in 2×SSC and 20% ethylene carbonate (Sigma-Aldrich) for 1 h in 37 C, washed 3×DEPC-PBS-Tween 20, and incubated with 0.03 µM snap-cooled fluorescently labelled DNA hairpins in amplification buffer (5×SSC, 0.1% Tween 20 and 10% dextran sulfate), as previously described for DNA HCR (Harry Choi et al. Next-generation in situ hybridization chain reaction: Higher gain, lower cost, greater durability. ACS Nano, 8 (5) pp: 4284-4294 (2014), DOI: 10.1021/nn405717p) for 1 h. For colon tissues, all RCA products were dual-stained with wild type- or mutant-specific hairpins and general hairpins that hybridised to all RCA products. Samples were then washed 3×5 min with 5×SSC-Tween 20. For imaging after the RCA part only and after the HCR-RCA, nuclei were stained with DAPI (Sigma-Aldrich) and slides were mounted using Slowfade mounting media (ThermoFischer). LNA modified primers for reverse transcription (Qiagen), padlock probe sequences, PLP detection probes and HCR-initiator sequences (Integrated DNA Technologies) are listed in Table 1, +X indicates an LNA residue, e.g. +T is a thymine LNA nucleotide, +A is an adenine LNA nucleotide, etc. The hairpin probes B1-B5 (Table 2) were acquired from Molecular Technologies, Caltech, United States.

TABLE 1

| SEQ ID NO | Probe | Sequence |
|---|---|---|
| 1 | RT-primer KRAS | CC+TC+TA+TT+GT+TGG+AT+CATAT TCGTC |
| 2 | RT-primer ACTB | C+GG+GC+GG+CG+GATCGGCAAAG |

TABLE 1-continued

| SEQ ID NO | Probe | Sequence |
|---|---|---|
| 3 | Padlock probe_KRASwt_G12 | TGGCGTAGGCAAGAGAGTAGCCGTG ACTATCGACTCCTCAATGCTGCTGCT GTACTACGGTAGTTGGAGCTGG |
| 4 | Padlock probe_KRASmut_G12D | TGGCGTAGGCAAGAGCCTCAATGCA CATGTTTGGCTCCAGTCGGAAGTAC TACTCTCTGGTAGTTGGAGCTGA |
| 5 | Padlock probe_ACTB | AGCCTCGCCTTTGCCTCCTCTATGAT TACTGACTGCGTCTATTTAGTGGAG CCACGACTATCTTCTTTCGCCCCGCG AGCACAG |
| 6 | RCA detection probe KRASwt | CCTCAATGCTGCTGCTGTACTAC |
| 7 | RCA detection probe KRASmut | AGTCGGAAGTACTACTCTCT |
| 8 | RCA detection probe ACTB | TGCGTCTATTTAGTGGAGCC |
| 9 | HCR-initiator_KRASwt_P1_B2 | AGCTCAGTCCATCCTCGTAATCAAT GCTGCTGCTGTACTAC |
| 10 | HCR-initiator_KRASwt_P2_B2 | AGTAGCCGTGACTATCGACTAAAAA TCCTCATCAATCATC |
| 11 | HCR-initiator_KRASmut_P1_B4 | CACATTTACAGACCTCAAATAGTCG GAAGTACTACTCTCT |
| 12 | HCR-initiator_KRASmut_P2_B4 | CCTCAATGCACATGTTTGGCTATCCT ACCTCCAACTCTCAC |
| 13 | HCR-initiator_KRASgeneral_P1_B5 | CTCACTCCCAATCTCTATAA GGCGTAGGCAAGAGTCCTAG |
| 14 | HCR-initiator KRASgeneral_P2 B5 | TCAAAGGGTAGTTGGAGCTGAACTA CCCTACAAATCCAAT |
| 15 | HCR-initiator_ACTB_P1_B3 | GTCCCTGCCTCTATATCTTTTGCCTC CTCTATGATTACTGACTGC |
| 16 | HCR-initiator_ACTB_P2_B3 | CGCCCCGCGAGCACAGAGCCTCGCC TTCCACTCAACTTTAACCCG |

TABLE 2

Hairpin systems:

B1_AF488
B2_AF546
B3_AF594
B4_AF647
B5_AF750

HCR-RCA for Rapid and Highly Multiplexable Single Molecule Detection Through Sequential Combinatorial Labelling The RCA part was performed as described above except that random decamers (Integrated DNA Technologies) were used for the reverse transcription. For multiplexed HCR-RCA, HCR-initiators v.2 (length of the RCA-hybridizing part was 14-15 nt) were used to enable efficient stripping of the HCR signals between imaging cycles. Here, target-specific HCR-initiators (and general initiators for the combinatorial labelling) were hybridized for 1 h and HCR was performed for 2 h. Multiplexing was achieved by combinatorial labelling (all targets were imaged in every cycle, for 3 cycles). Stripping of the HCR signals were done with 100% formamide (Sigma-Aldrich) for 1 min followed by 2×5 min. Padlock probes and HCR-initiator sequences are listed in Table 3. Table 3 shows padlock probes and HCR-initiator sequences used for multiplexed detection, padlock probe sequences for all genes are listed including the initiator sequences.

TABLE 3

| SEQ ID NO | Probe | Sequence |
|---|---|---|
| 17 | Padlock probe_Cplx3 | GTTTTCTTTCAGACAGAATCTGCGTCTATTTAGT GGAGCCACTGCTATCTACGTAGCTAGACGTTGT CTTAGTTGGTATTATTGTCATTTT |
| 18 | Padlock probe_Rprm | AGCAACGCAAACCTGTCTGCGTCTATTTAGTGG AGCCACACCTATCTAGCTAGCTACTCGTTGTCCA CCATCACGGACCG |

TABLE 3-continued

| SEQ ID NO | Probe | Sequence |
|---|---|---|
| 19 | Padlock probe_Rasgrf2 | AGCTCCCGTGCCAACTGCGTCTATTTAGTGGAG CCCACACTATCTATATAGCTACGAGTTGTCATG AATTATGCCGACATC |
| 20 | Padlock probe_Plcxd2_345 | ATACCCTCACCATCTTCTGCGTCTATTTAGTGGA GCCGAAACTATCTCAGTAGCTACCTGTTGTCTCA TTGTGTAGGAGTGC |
| 21 | Padlock probe_Plcxd2_654 | TGTCCCTTCTACAAGCATGCGTCTATTTAGTGGA GCCGGCCCTATCTCCTTAGCTACAGGTTGTCGTT CTCATTTTCTACCAC |
| 22 | Padlock probe_Sulf2_563 | CCTACACCAACAATGAGATGCGTCTATTTAGTG GAGCCCAACCTATCTCGATAGCTAATAGTTGTC CGTCCACAACCACAACA |
| 23 | Padlock probe_Pcp4_872 | GGGCAGAAGAAAGTCCTGCGTCTATTTAGTGGA GCCAAGACTATCTCTCTAGCTAAGCGTTGTCAC GTCAGGAGATAATGAT |
| 24 | Padlock probe_Zdhhc23_781 | CCTGGATTCTTCTTGGTGCGTCTATTTAGTGGAG CCTGGTCTATCTGACTAGCTAACGGTTGTCTGTC ATTGCTGAGGTAG |
| 25 | General_HCR-initiator_B5 | CTCACTCCCAATCTCTATCTACCCTACAAATCCA ATAAAAATGCGTCTATTTAGTGGAGCC |
| 26 | cycle1_HCR-initiator_B3 | TAGCTAGACGTTGTTAAAAAAAGTCTAATCCGT CCCTGCCTCTATATCTCCACTC |
| 27 | cycle1_HCR-initiator_B3 | TAGCTACTCGTTGTTAAAAAAAGTCTAATCCGT CCCTGCCTCTATATCTCCACTC |
| 28 | cycle1_HCR-initiator_B4 | TAGCTACGAGTTGTATTTTCACATTTACAGACCT CAACCTACCTCCAACTCTCAC |
| 29 | cycle1_HCR-initiator_B3 | TAGCTACCTGTTGTTAAAAAAAGTCTAATCCGT CCCTGCCTCTATATCTCCACTC |
| 30 | cycle1_HCR-initiator_B3 | TAGCTACAGGTTGTTAAAAAAAGTCTAATCCGT CCCTGCCTCTATATCTCCACTC |
| 31 | cycle1_HCR-initiator_B4 | TAGCTAATAGTTGTATTTTCACATTTACAGACCT CAACCTACCTCCAACTCTCAC |
| 32 | cycle1_HCR-initiator_B4 | TAGCTAAGCGTTGTATTTTCACATTTACAGACCT CAACCTACCTCCAACTCTCAC |
| 33 | cycle1_HCR-initiator_B4 | TAGCTAACGGTTGTATTTTCACATTTACAGACCT CAACCTACCTCCAACTCTCAC |
| 34 | cycle2_HCR-initiator_B1 | TAGCTAGACGTTGTATATAGCATTCTTTCTTGAG GAGGGCAGCAAACGGGAAGAG |
| 35 | cycle2_HCR-initiator_B3 | TAGCTACTCGTTGTTAAAAAAAGTCTAATCCGT CCCTGCCTCTATATCTCCACTC |
| 36 | cycle2_HCR-initiator_B1 | TAGCTACGAGTTGTATATAGCATTCTTTCTTGAG GAGGGCAGCAAACGGGAAGAG |
| 37 | cycle2_HCR-initiator_B4 | TAGCTACCTGTTGTATTTTCACATTTACAGACCT CAACCTACCTCCAACTCTCAC |
| 38 | cycle2_HCR-initiator_B2 | TAGCTACAGGTTGTAAAAAAGCTCAGTCCATCC TCGTAAATCCTCATCAATCATC |
| 39 | cycle2_HCR-initiator_B4 | TAGCTAATAGTTGTATTTTCACATTTACAGACCT CAACCTACCTCCAACTCTCAC |
| 40 | cycle2_HCR-initiator_B3 | TAGCTAAGCGTTGTTAAAAAAAGTCTAATCCGT CCCTGCCTCTATATCTCCACTC |
| 41 | cycle2_HCR-initiator_B2 | TAGCTAACGGTTGTAAAAAAGCTCAGTCCATCC TCGTAAATCCTCATCAATCATC |
| 42 | cycle3_HCR-initiator_B3 | TAGCTAGACGTTGTTAAAAAAAGTCTAATCCGT CCCTGCCTCTATATCTCCACTC |

TABLE 3-continued

| SEQ ID NO | Probe | Sequence |
|---|---|---|
| 43 | cycle3_HCR-initiator_B1 | TAGCTACTCGTTGTATATAGCATTCTTTCTTGAG GAGGGCAGCAAACGGGAAGAG |
| 44 | cycle3_HCR-initiator_B4 | TAGCTACGAGTTGTATTTTCACATTTACAGACCT CAACCTACCTCCAACTCTCAC |
| 45 | cycle3_HCR-initiator_B2 | TAGCTACCTGTTGTAAAAAAGCTCAGTCCATCC TCGTAAATCCTCATCAATCATC |
| 46 | cycle3_HCR-initiator_B4 | TAGCTACAGGTTGTATTTTCACATTTACAGACCT CAACCTACCTCCAACTCTCAC |
| 47 | cycle3_HCR-initiator_B1 | TAGCTAATAGTTGTATATAGCATTCTTTCTTGAG GAGGGCAGCAAACGGGAAGAG |
| 48 | cycle3_HCR-initiator_B2 | TAGCTAAGCGTTGTAAAAAAGCTCAGTCCATCC TCGTAAATCCTCATCAATCATC |
| 49 | cycle3_HCR-initiator_B3 | TAGCTAACGGTTGTTAAAAAAAGTCTAATCCGT CCCTGCCTCTATATCTCCACTC |

Imaging

Images were acquired with an automated Zeiss Axioplan II epifluorescence microscope (Zeiss, Oberkochen, Germany) using z-stack and a tile overlap of 10%. For the direct detection of KRAS wild type and mutant, images were scanned with a 20× objective. For the multiplexed HCR-RCA, images were scanned with a 10× objective.

Image Analysis

Orthogonal projections and stitching of tiles were done with the ZEN software (Zeiss). Co-localization analysis of dual-labelled signals. For the multiplexed combinatorial and non-combinatorial labelling, images from the cycles were aligned (using the general stain for the combinatorial and the nuclei stain for the non-combinatorial labelling) and decoded using Cellprofiler (Broad Institute, MA, United States) and an in-house Matlab script (Mathworks, Sweden). A quality score for correct signal was set, as previously described (Ke et al. In situ sequencing for RNA analysis in preserved tissue and cells. Nat Methods 10, 857-860 (2013) doi:10.1038/nmeth.2563). For comparison of numbers of signals and signal intensities, RCA only and HCR-RCA signals were identified, counted and maximum intensities were measured using Cellprofiler.

Median-Modelled Signals and Signal to Noise (SNR) Ratios

Signal intensities were measured along the equator line of signals using ImageJ (Rasband, W. S., ImageJ, U. S. National Institutes of Health, Bethesda, Maryland, USA, https://imagej.nih.gov/ij/, 1997-2018). Lines of 30 pixels were used and for each signal the centre of the line corresponded to the centre of the signal. The 4 end pixels on both sides of the 30 pixel line of signals were used to calculate the median local background. Median-modelled signals were generated by subtracting the median local background from the median intensity values along the line, to generate the median intensities for 100 signals along the 30 pixel equator line. For SNR, median intensity values along the equator line were divided with the median local background. The median SNR for 100 signals along the 30 pixel equator line were then used to illustrate the SNR for RCA only as well as HCR-RCA.

Results

HCR-RCA: Hybridization Chain Reaction (HCR) on Rolling Circle Amplified Padlock Probes Here, we demonstrate further amplification of RCA products through Hybridization Chain Reaction. HCR initiators are hybridized to the RCA products and initiate HCR of fluorophore-labelled metastable HCR hairpins (FIG. 1). In the BJhTERT cell line, the combined HCR-RCA increased signal intensities (FIGS. 2A-2B and FIG. 3A) and the signal-to-noise ratio (SNR) 1.4-fold (FIG. 3B) and also enabled identification of 15% more signals, as compared to RCA only (FIG. 3C).

The resulting strong signal intensity of the HCR-RCA allows for highly sensitive detection of RNA transcripts with single nucleotide resolution. Here, we demonstrate its application for strongly improved quantification of wild-type and mutant KRAS transcripts in autofluorescent colon cancer tissue samples, and for ultrafast highly multiplexed single cell gene expression profiling in mouse tissue sections by sequential HCR labelling.

Figures 4A, 4B, 4C, 4D, 4E:
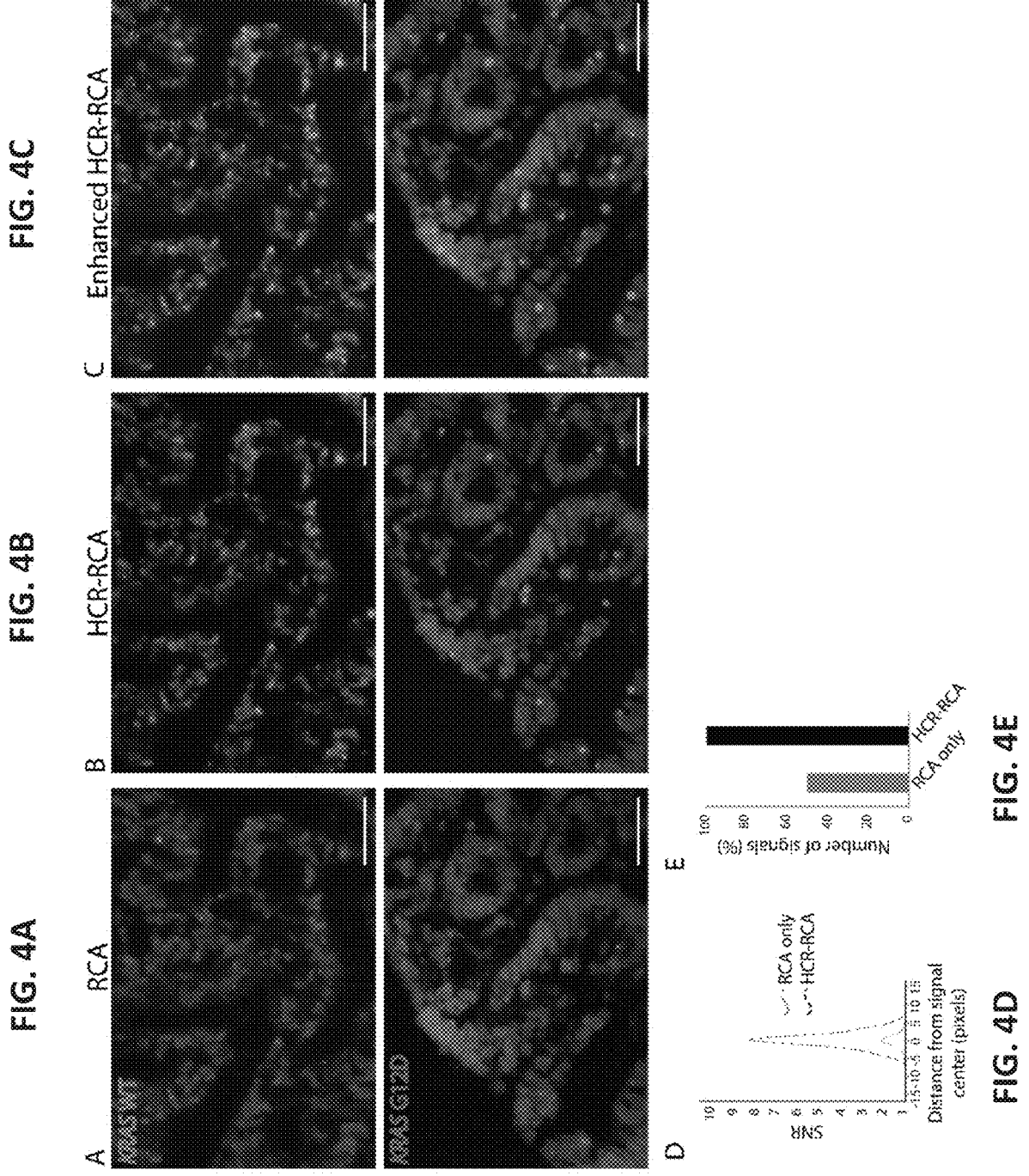
FIGS. 4A-4E show a representative comparison of images and signals between RCA only and HCR-RCA when imaging KRAS wild type and KRAS mutant detection in autofluorescent colon cancer tissue sections.

HCR-RCA Increases Signal/Noise and Enables Accurate In Situ Mutation Detection in Autofluorescent Colon Cancer Tissues The HCR-RCA combination significantly increases the signal/noise ratio by further amplifying the local density of fluorescently labelled reporter oligonucleotides within RCA products through HCR elevating the signal intensity far above tissue autofluorescence (FIGS. 4A-4E). HCR-RCA was applied to a padlock probe-RCA mediated KRAS mutation detection assay in fixed colon cancer tissues with strong autofluorescence (FIGS. 4A-4E). With RCA only, fluorescent signals of RCA products were difficult to distinguish from the strong autofluorescent background and lead to false positive detection of mutations (FIG. 4A, RCA only). When further amplifying the same RCA products with HCR-RCA, the signal intensity significantly increased above background fluorescence (FIG. 4B, HCR-RCA) and turned the same RCA mutation assay on the same tissue sample into a highly precise mutation detection with very low false positive rate. The combination of the highly specific padlock probe ligation assay and signal amplification through HCR-RCA enables highly specific tissue mutation profiling even in difficult tissue samples, further improving the diagnostic potential of this assay format.

Figures 5A, 5B, 5C, 5D:
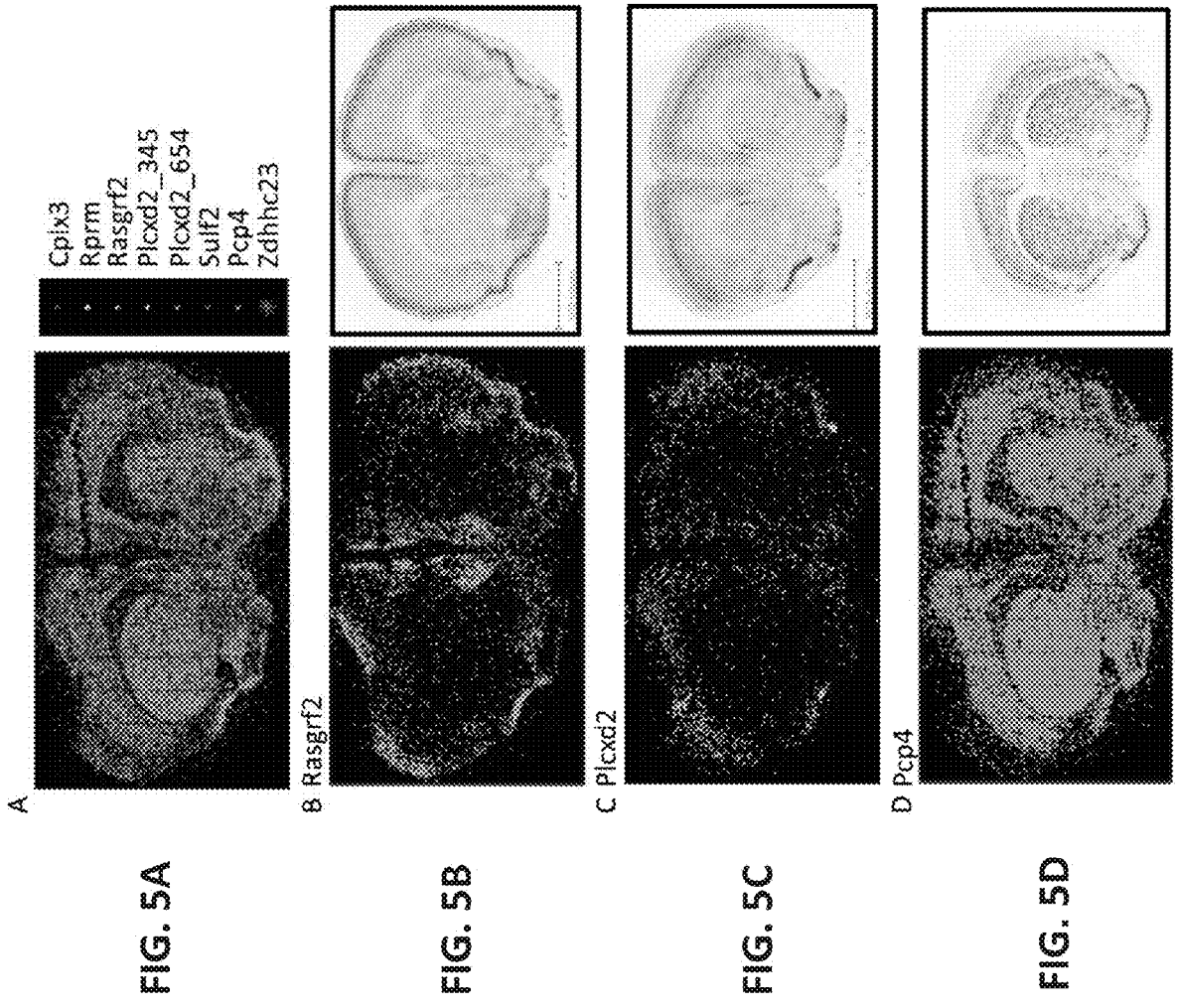
FIGS. 5A-5D show a representative multiplexed HCR-RCA in mouse brain tissue sections.

Rapid and Highly Multiplexable HCR-RCA by Sequential Combinatorial and Non-Combinatorial Labelling Multiplexed HCR-RCA was performed by detecting 8 genes simultaneously in mouse brain tissue sections (FIG. 5A). Initiator probes were hybridized in three cycles with a specific colour scheme for each gene. The expression patterns for four of the detected genes were compared with in situ hybridization experiments (ISH) from the Allen Brain Atlas with good correlation (FIGS. 5B-5D, right). One of the gene targets was detected with two separate probes, showing overlapping expression patterns (FIG. 5C).

Changes in Signal Intensity with Different Time of RCA or HCR

Figure 6A:
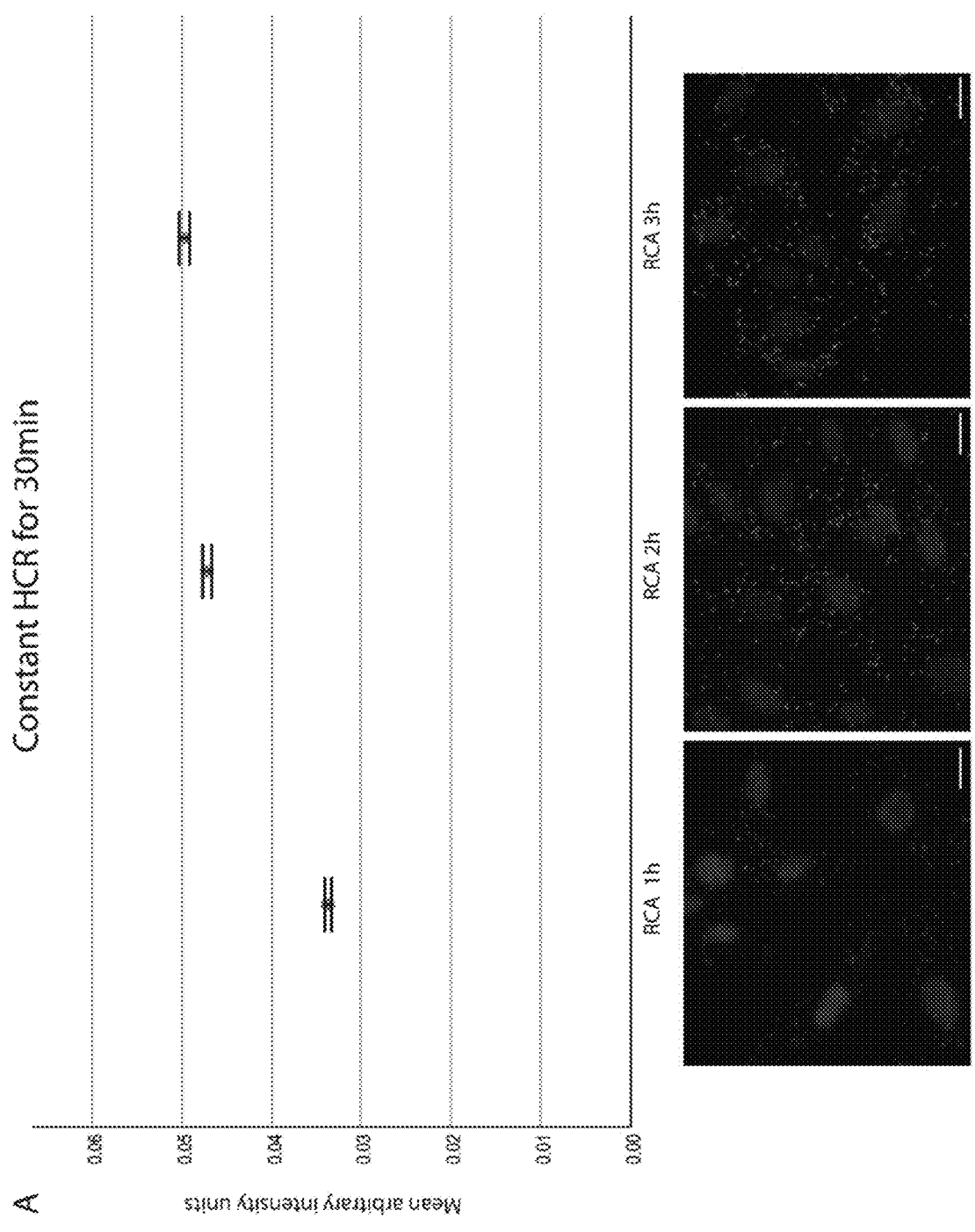
FIGS. 6A-6B show representative changes in signals intensity with different time of RCA or HCR.
Figure 6B:
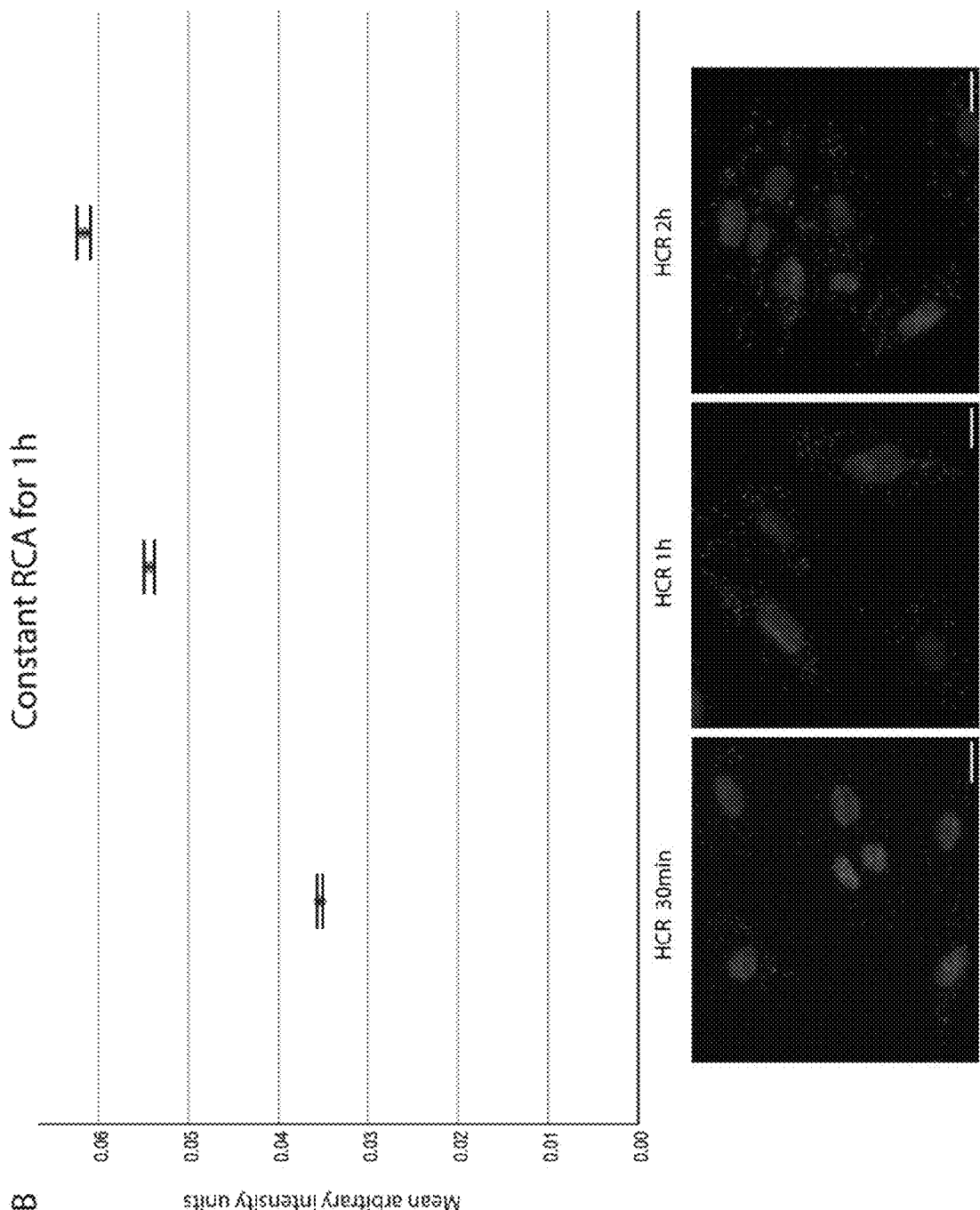

HCR-RCA to detect the gene ACTB using Alexa Fluor® 594 (fluorescent moiety) in BJhTERT cell line were performed. The time allowed for the HCR reaction was kept constant (30 minutes), and the time for the RCA reaction was varied (1 hr, 2 hrs or 3 hrs). The results are shown in FIG. 6A. Similarly, the same reaction was performed where the time for the RCA reaction (1 hr) was kept constant and the time for the HCR reaction was varied (30 mins, 1 hr, or 2 hrs). These results are shown in FIG. 6B. It can be seen that, in general, increased reaction times results in increased mean signal intensity. Furthermore, the highest signal intensity was obtained with a fixed 1 hr RCA reaction, and a 2 hr HCR reaction, which gave greater signal intensity than even the 30 min HCR and 3 hr RCA combination.

Figure 7:
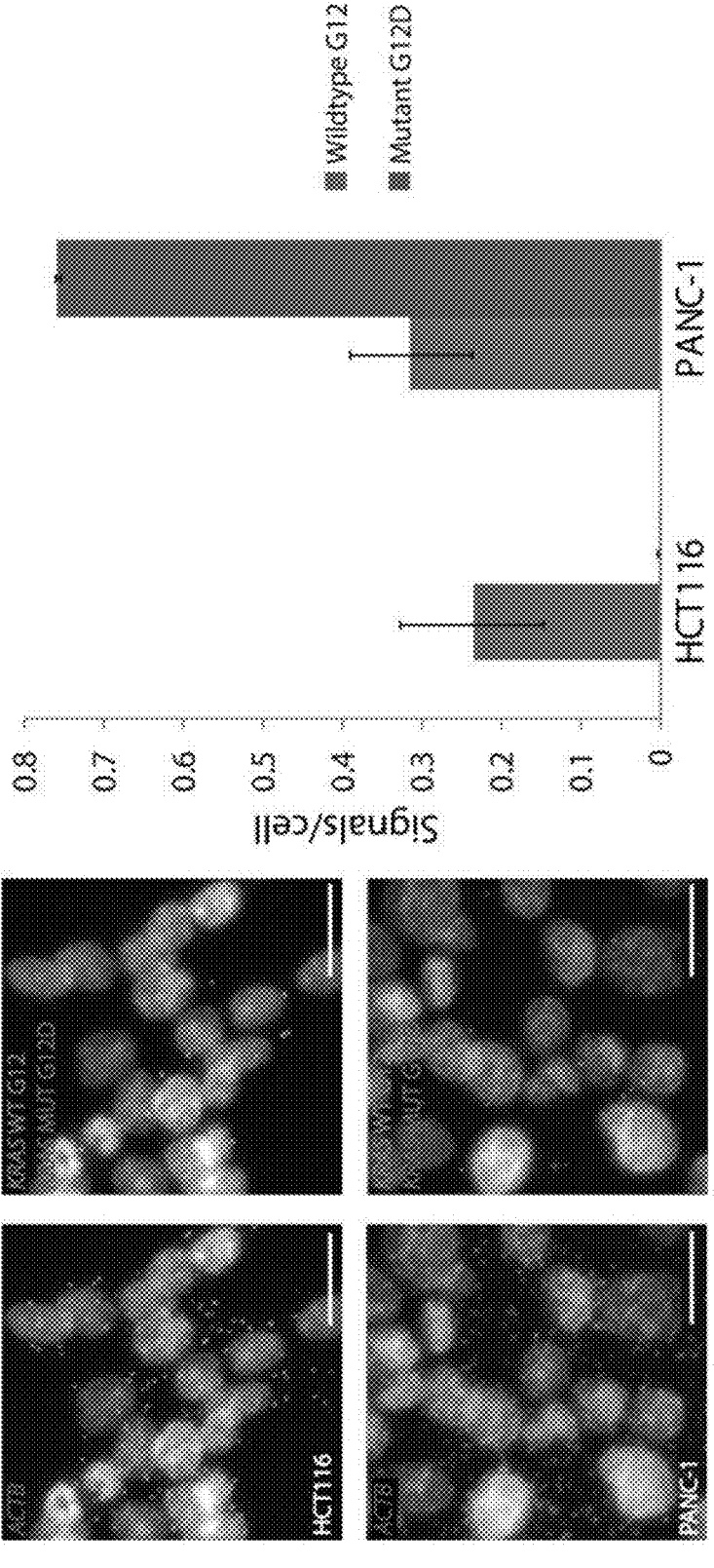
FIG. 7 shows a representative validation of specificity for KRAS wild type and KRAS mutant detection in cell lines.

Validation of Specificity for KRAS Wild Type and Mutant Detection in Cancer Cell Lines The specificity of the HCR-RCA method was validated using the colon cancer cell line HCT116 (which is wild type at codon G12 of the KRAS gene), and the pancreatic cancer cell line PANC-1 (which has the mutant G12D codon in the KRAS gene). It can be seen from FIG. 7 that almost no mutant signal was detected in the HCT116 cell line, where the wild type codon is present; and, conversely, that a significant mutant signal was observed in respect of the PANC-1 cell line, featuring the G12D mutant.

---

The invention claimed is:

1. A method for detecting an analyte in a sample, comprising:
   (i) providing a rolling circle amplification product (RCP) in the sample, wherein the RCP comprises multiple repeat copies of a barcode sequence indicative of the analyte;
   (ii) performing a hybridization chain reaction (HCR) wherein the HCR is performed using HCR monomers in the form of hairpins, wherein the HCR is initiated by an HCR initiator which hybridizes to the RCP at the barcode sequence; and
   (iii) detecting the product of the HCR at a location in the sample, thereby detecting the analyte at the location in the sample.

2. The method of claim 1, wherein the analyte is a nucleic acid molecule, a lipid or a protein.

3. The method of claim 2, wherein the nucleic acid molecule is DNA or RNA.

4. The method of claim 1, wherein the sample comprises cells.

5. The method of claim 4, wherein the cells are immobilized and/or fixed.

6. The method of claim 1, wherein the sample is a tissue sample and the analyte is detected in situ in the tissue sample.

7. The method of claim 1, wherein the analyte is detected in single cells.

8. The method of claim 1, wherein the analyte is a nucleic acid molecule, and wherein a circularizable probe comprising a complement of the barcode sequence is hybridized to the analyte and is circularized to form a rolling circle amplification (RCA) template, which is subjected to RCA to form the RCP.

9. The method of claim 1, wherein the method is used to detect multiple analytes in the sample, and at least one RCP is provided for each analyte.

10. The method of claim 1, wherein the HCR monomers comprise first HCR monomers and second HCR monomers, wherein the first HCR monomers comprise a toehold region which is complementary to the HCR initiator and to the interacting region in the second HCR monomers, and the toehold region in the second HCR monomers is complementary to the interacting region in the first HCR monomers.

11. The method of claim 10, wherein at least a fraction of at least one of the HCR monomers is labelled with a detectable label.

12. The method of claim 9, wherein for each RCP, multiple sequential HCRs are performed, and the respective HCR products are detected together to provide for detection of the analyte.

13. The method of claim 12, wherein the sequential HCRs are performed using differentially labelled HCR monomer sets, such that each RCP is combinatorially labelled to detect the analyte.

14. The method of claim 1, wherein the analyte is one of multiple analytes in the sample, wherein the multiple analytes are detected by providing an RCP for each analyte, and wherein the method is performed sequentially in cycles and a different set of RCPs is detected in each cycle, to detect a different set of analytes.

15. The method of claim 14, wherein in a first cycle, a first set of RCPs is detected using a first set of HCR initiators each specific for a different member of the first set of RCPs and the HCR products are removed after the detection, and in a second or subsequent cycle, a second or subsequent set of RCPs is detected using a second or subsequent set of HCR initiators each specific for a different member of the first or subsequent set of RCPs, and the HCR products are removed after the detection.

16. The method of claim 15, wherein in each cycle the same sets of HCR monomers are used.

17. The method of claim 1, wherein the barcode sequence is between 5 and 50 nucleotides in length.

18. The method of claim 1, wherein the rolling circle amplification for generating the RCP is performed for no more than 3 hours.

19. The method of claim 1, wherein the rolling circle amplification for generating the RCP is performed for no more than 2 hours.

20. The method of claim 1, wherein the rolling circle amplification for generating the RCP is performed for between 2 hours and 3 hours, and the HCR is performed for at least 30 minutes.

21. The method of claim 1, wherein the rolling circle amplification for generating the RCP is performed for about 2 hours, and the HCR is performed for about 1 hour.

\* \* \* \* \*

SEQUENCE LISTING

```
<160> NUMBER OF SEQ ID NOS: 49

<210> SEQ ID NO 1
<211> LENGTH: 25
<212> TYPE: DNA
<213> ORGANISM: Artificial Sequence
<220> FEATURE:
<223> OTHER INFORMATION: Synthetic construct

<400> SEQUENCE: 1
cctctattgt tggatcatat tcgtc                                           25

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
cgggcggcgg atcggcaaag                                                 20

<210> SEQ ID NO 3
<211> LENGTH: 73
<212> TYPE: DNA
<213> ORGANISM: Artificial Sequence
<220> FEATURE:
<223> OTHER INFORMATION: Synthetic construct

<400> SEQUENCE: 3
tggcgtaggc aagagagtag ccgtgactat cgactcctca atgctgctgc tgtactacgg    60
tagttggagc tgg                                                        73

<210> SEQ ID NO 4
<211> LENGTH: 73
<212> TYPE: DNA
<213> ORGANISM: Artificial Sequence
<220> FEATURE:
<223> OTHER INFORMATION: Synthetic construct

<400> SEQUENCE: 4
tggcgtaggc aagagcctca atgcacatgt ttggctccag tcggaagtac tactctctgg    60
tagttggagc tga                                                        73

<210> SEQ ID NO 5
<211> LENGTH: 84
<212> TYPE: DNA
```

```
<213> ORGANISM: Artificial Sequence
<220> FEATURE:
<223> OTHER INFORMATION: Synthetic construct

<400> SEQUENCE: 5
agcctcgcct ttgcctcctc tatgattact gactgcgtct atttagtgga gccacgacta      60
tcttctttcg ccccgcgagc acag                                             84

<210> SEQ ID NO 6
<211> LENGTH: 23
<212> TYPE: DNA
<213> ORGANISM: Artificial Sequence
<220> FEATURE:
<223> OTHER INFORMATION: Synthetic construct

<400> SEQUENCE: 6
cctcaatgct gctgctgtac tac                                              23

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
agtcggaagt actactctct                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
tgcgtctatt tagtggagcc                                                  20

<210> SEQ ID NO 9
<211> LENGTH: 41
<212> TYPE: DNA
<213> ORGANISM: Artificial Sequence
<220> FEATURE:
<223> OTHER INFORMATION: Synthetic construct

<400> SEQUENCE: 9
agctcagtcc atcctcgtaa tcaatgctgc tgctgtacta c                          41

<210> SEQ ID NO 10
<211> LENGTH: 40
<212> TYPE: DNA
<213> ORGANISM: Artificial Sequence
<220> FEATURE:
<223> OTHER INFORMATION: Synthetic construct

<400> SEQUENCE: 10
agtagccgtg actatcgact aaaaatcctc atcaatcatc                            40

<210> SEQ ID NO 11
<211> LENGTH: 40
<212> TYPE: DNA
<213> ORGANISM: Artificial Sequence
<220> FEATURE:
<223> OTHER INFORMATION: Synthetic construct

<400> SEQUENCE: 11
```

```
cacatttaca gacctcaaat agtcggaagt actactctct                           40

<210> SEQ ID NO 12
<211> LENGTH: 41
<212> TYPE: DNA
<213> ORGANISM: Artificial Sequence
<220> FEATURE:
<223> OTHER INFORMATION: Synthetic construct

<400> SEQUENCE: 12
cctcaatgca catgtttggc tatcctacct ccaactctca c                         41

<210> SEQ ID NO 13
<211> LENGTH: 40
<212> TYPE: DNA
<213> ORGANISM: Artificial Sequence
<220> FEATURE:
<223> OTHER INFORMATION: Synthetic construct

<400> SEQUENCE: 13
ctcactccca atctctataa ggcgtaggca agagtcctag                           40

<210> SEQ ID NO 14
<211> LENGTH: 40
<212> TYPE: DNA
<213> ORGANISM: Artificial Sequence
<220> FEATURE:
<223> OTHER INFORMATION: Synthetic construct

<400> SEQUENCE: 14
tcaaagggta gttggagctg aactacccta caaatccaat                           40

<210> SEQ ID NO 15
<211> LENGTH: 45
<212> TYPE: DNA
<213> ORGANISM: Artificial Sequence
<220> FEATURE:
<223> OTHER INFORMATION: Synthetic construct

<400> SEQUENCE: 15
gtccctgcct ctatatcttt tgcctcctct atgattactg actgc                     45

<210> SEQ ID NO 16
<211> LENGTH: 45
<212> TYPE: DNA
<213> ORGANISM: Artificial Sequence
<220> FEATURE:
<223> OTHER INFORMATION: Synthetic construct

<400> SEQUENCE: 16
cgccccgcga gcacagagcc tcgccttcca ctcaacttta acccg                     45

<210> SEQ ID NO 17
<211> LENGTH: 91
<212> TYPE: DNA
<213> ORGANISM: Artificial Sequence
<220> FEATURE:
<223> OTHER INFORMATION: Synthetic construct

<400> SEQUENCE: 17
gttttctttc agacagaatc tgcgtctatt tagtggagcc actgctatct acgtagctag     60
acgttgtctt agttggtatt attgtcattt t                                    91

<210> SEQ ID NO 18
```

```
<211> LENGTH: 80
<212> TYPE: DNA
<213> ORGANISM: Artificial Sequence
<220> FEATURE:
<223> OTHER INFORMATION: Synthetic construct

<400> SEQUENCE: 18
agcaacgcaa acctgtctgc gtctatttag tggagccaca cctatctagc tagctactcg      60
ttgtccacca tcacggaccg                                                  80

<210> SEQ ID NO 19
<211> LENGTH: 81
<212> TYPE: DNA
<213> ORGANISM: Artificial Sequence
<220> FEATURE:
<223> OTHER INFORMATION: Synthetic construct

<400> SEQUENCE: 19
agctcccgtg ccaactgcgt ctatttagtg gagcccacac tatctatata gctacgagtt      60
gtcatgaatt atgccgacat c                                                81

<210> SEQ ID NO 20
<211> LENGTH: 82
<212> TYPE: DNA
<213> ORGANISM: Artificial Sequence
<220> FEATURE:
<223> OTHER INFORMATION: Synthetic construct

<400> SEQUENCE: 20
ataccctcac catcttctgc gtctatttag tggagccgaa actatctcag tagctacctg      60
ttgtctcatt gtgtaggagt gc                                               82

<210> SEQ ID NO 21
<211> LENGTH: 83
<212> TYPE: DNA
<213> ORGANISM: Artificial Sequence
<220> FEATURE:
<223> OTHER INFORMATION: Synthetic construct

<400> SEQUENCE: 21
tgtcccttct acaagcatgc gtctatttag tggagccggc cctatctcct tagctacagg      60
ttgtcgttct cattttctac cac                                              83

<210> SEQ ID NO 22
<211> LENGTH: 83
<212> TYPE: DNA
<213> ORGANISM: Artificial Sequence
<220> FEATURE:
<223> OTHER INFORMATION: Synthetic construct

<400> SEQUENCE: 22
cctacaccaa caatgagatg cgtctattta gtggagccca acctatctcg atagctaata      60
gttgtccgtc cacaaccaca aca                                              83

<210> SEQ ID NO 23
<211> LENGTH: 82
<212> TYPE: DNA
<213> ORGANISM: Artificial Sequence
<220> FEATURE:
<223> OTHER INFORMATION: Synthetic construct

<400> SEQUENCE: 23
gggcagaaga aagtcctgcg tctatttagt ggagccaaga ctatctctct agctaagcgt      60
```

-continued tgtcacgtca ggagataatg at                                    82

<210> SEQ ID NO 24
<211> LENGTH: 81
<212> TYPE: DNA
<213> ORGANISM: Artificial Sequence
<220> FEATURE:
<223> OTHER INFORMATION: Synthetic construct

<400> SEQUENCE: 24
cctggattct tcttggtgcg tctatttagt ggagcctggt ctatctgact agctaacggt    60
tgtctgtcat tgctgaggta g                                      81

<210> SEQ ID NO 25
<211> LENGTH: 61
<212> TYPE: DNA
<213> ORGANISM: Artificial Sequence
<220> FEATURE:
<223> OTHER INFORMATION: Synthetic construct

<400> SEQUENCE: 25
ctcactccca atctctatct accctacaaa tccaataaaa atgcgtctat ttagtggagc    60
c                                                           61

<210> SEQ ID NO 26
<211> LENGTH: 55
<212> TYPE: DNA
<213> ORGANISM: Artificial Sequence
<220> FEATURE:
<223> OTHER INFORMATION: Synthetic construct

<400> SEQUENCE: 26
tagctagacg ttgttaaaaa aagtctaatc cgtccctgcc tctatatctc cactc           55

<210> SEQ ID NO 27
<211> LENGTH: 55
<212> TYPE: DNA
<213> ORGANISM: Artificial Sequence
<220> FEATURE:
<223> OTHER INFORMATION: Synthetic construct

<400> SEQUENCE: 27
tagctactcg ttgttaaaaa aagtctaatc cgtccctgcc tctatatctc cactc           55

<210> SEQ ID NO 28
<211> LENGTH: 55
<212> TYPE: DNA
<213> ORGANISM: Artificial Sequence
<220> FEATURE:
<223> OTHER INFORMATION: Synthetic construct

<400> SEQUENCE: 28
tagctacgag ttgtattttc acatttacag acctcaacct acctccaact ctcac           55

<210> SEQ ID NO 29
<211> LENGTH: 55
<212> TYPE: DNA
<213> ORGANISM: Artificial Sequence
<220> FEATURE:
<223> OTHER INFORMATION: Synthetic construct

<400> SEQUENCE: 29
tagctacctg ttgttaaaaa aagtctaatc cgtccctgcc tctatatctc cactc           55

-continued

```
<210> SEQ ID NO 30
<211> LENGTH: 55
<212> TYPE: DNA
<213> ORGANISM: Artificial Sequence
<220> FEATURE:
<223> OTHER INFORMATION: Synthetic construct

<400> SEQUENCE: 30
tagctacagg ttgttaaaaa aagtctaatc cgtccctgcc tctatatctc cactc        55

<210> SEQ ID NO 31
<211> LENGTH: 55
<212> TYPE: DNA
<213> ORGANISM: Artificial Sequence
<220> FEATURE:
<223> OTHER INFORMATION: Synthetic construct

<400> SEQUENCE: 31
tagctaatag ttgtattttc acatttacag acctcaacct acctccaact ctcac        55

<210> SEQ ID NO 32
<211> LENGTH: 55
<212> TYPE: DNA
<213> ORGANISM: Artificial Sequence
<220> FEATURE:
<223> OTHER INFORMATION: Synthetic construct

<400> SEQUENCE: 32
tagctaagcg ttgtattttc acatttacag acctcaacct acctccaact ctcac        55

<210> SEQ ID NO 33
<211> LENGTH: 55
<212> TYPE: DNA
<213> ORGANISM: Artificial Sequence
<220> FEATURE:
<223> OTHER INFORMATION: Synthetic construct

<400> SEQUENCE: 33
tagctaacgg ttgtattttc acatttacag acctcaacct acctccaact ctcac        55

<210> SEQ ID NO 34
<211> LENGTH: 55
<212> TYPE: DNA
<213> ORGANISM: Artificial Sequence
<220> FEATURE:
<223> OTHER INFORMATION: Synthetic construct

<400> SEQUENCE: 34
tagctagacg ttgtatatag cattctttct tgaggagggc agcaaacggg aagag        55

<210> SEQ ID NO 35
<211> LENGTH: 55
<212> TYPE: DNA
<213> ORGANISM: Artificial Sequence
<220> FEATURE:
<223> OTHER INFORMATION: Synthetic construct

<400> SEQUENCE: 35
tagctactcg ttgttaaaaa aagtctaatc cgtccctgcc tctatatctc cactc        55

<210> SEQ ID NO 36
<211> LENGTH: 55
<212> TYPE: DNA
<213> ORGANISM: Artificial Sequence
<220> FEATURE:
<223> OTHER INFORMATION: Synthetic construct
```

<400> SEQUENCE: 36
tagctacgag ttgtatatag cattctttct tgaggagggc agcaaacggg aagag          55

<210> SEQ ID NO 37
<211> LENGTH: 55
<212> TYPE: DNA
<213> ORGANISM: Artificial Sequence
<220> FEATURE:
<223> OTHER INFORMATION: Synthetic construct

<400> SEQUENCE: 37
tagctacctg ttgtattttc acatttacag acctcaacct acctccaact ctcac          55

<210> SEQ ID NO 38
<211> LENGTH: 55
<212> TYPE: DNA
<213> ORGANISM: Artificial Sequence
<220> FEATURE:
<223> OTHER INFORMATION: Synthetic construct

<400> SEQUENCE: 38
tagctacagg ttgtaaaaaa gctcagtcca tcctcgtaaa tcctcatcaa tcatc          55

<210> SEQ ID NO 39
<211> LENGTH: 55
<212> TYPE: DNA
<213> ORGANISM: Artificial Sequence
<220> FEATURE:
<223> OTHER INFORMATION: Synthetic construct

<400> SEQUENCE: 39
tagctaatag ttgtattttc acatttacag acctcaacct acctccaact ctcac          55

<210> SEQ ID NO 40
<211> LENGTH: 55
<212> TYPE: DNA
<213> ORGANISM: Artificial Sequence
<220> FEATURE:
<223> OTHER INFORMATION: Synthetic construct

<400> SEQUENCE: 40
tagctaagcg ttgttaaaaa aagtctaatc cgtccctgcc tctatatctc cactc          55

<210> SEQ ID NO 41
<211> LENGTH: 55
<212> TYPE: DNA
<213> ORGANISM: Artificial Sequence
<220> FEATURE:
<223> OTHER INFORMATION: Synthetic construct

<400> SEQUENCE: 41
tagctaacgg ttgtaaaaaa gctcagtcca tcctcgtaaa tcctcatcaa tcatc          55

<210> SEQ ID NO 42
<211> LENGTH: 55
<212> TYPE: DNA
<213> ORGANISM: Artificial Sequence
<220> FEATURE:
<223> OTHER INFORMATION: Synthetic construct

<400> SEQUENCE: 42
tagctagacg ttgttaaaaa aagtctaatc cgtccctgcc tctatatctc cactc          55

<210> SEQ ID NO 43

-continued

```
<211> LENGTH: 55
<212> TYPE: DNA
<213> ORGANISM: Artificial Sequence
<220> FEATURE:
<223> OTHER INFORMATION: Synthetic construct

<400> SEQUENCE: 43
tagctactcg ttgtatatag cattctttct tgaggagggc agcaaacggg aagag        55

<210> SEQ ID NO 44
<211> LENGTH: 55
<212> TYPE: DNA
<213> ORGANISM: Artificial Sequence
<220> FEATURE:
<223> OTHER INFORMATION: Synthetic construct

<400> SEQUENCE: 44
tagctacgag ttgtattttc acatttacag acctcaacct acctccaact ctcac        55

<210> SEQ ID NO 45
<211> LENGTH: 55
<212> TYPE: DNA
<213> ORGANISM: Artificial Sequence
<220> FEATURE:
<223> OTHER INFORMATION: Synthetic construct

<400> SEQUENCE: 45
tagctacctg ttgtaaaaaa gctcagtcca tcctcgtaaa tcctcatcaa tcatc        55

<210> SEQ ID NO 46
<211> LENGTH: 55
<212> TYPE: DNA
<213> ORGANISM: Artificial Sequence
<220> FEATURE:
<223> OTHER INFORMATION: Synthetic construct

<400> SEQUENCE: 46
tagctacagg ttgtattttc acatttacag acctcaacct acctccaact ctcac        55

<210> SEQ ID NO 47
<211> LENGTH: 55
<212> TYPE: DNA
<213> ORGANISM: Artificial Sequence
<220> FEATURE:
<223> OTHER INFORMATION: Synthetic construct

<400> SEQUENCE: 47
tagctaatag ttgtatatag cattctttct tgaggagggc agcaaacggg aagag        55

<210> SEQ ID NO 48
<211> LENGTH: 55
<212> TYPE: DNA
<213> ORGANISM: Artificial Sequence
<220> FEATURE:
<223> OTHER INFORMATION: Synthetic construct

<400> SEQUENCE: 48
tagctaagcg ttgtaaaaaa gctcagtcca tcctcgtaaa tcctcatcaa tcatc        55

<210> SEQ ID NO 49
<211> LENGTH: 55
<212> TYPE: DNA
<213> ORGANISM: Artificial Sequence
```

-continued

```
<220> FEATURE:
<223> OTHER INFORMATION: Synthetic construct

<400> SEQUENCE: 49
tagctaacgg ttgttaaaaa aagtctaatc cgtccctgcc tctatatctc cactc          55
```